United States Patent [19]
Williams et al.

[11] Patent Number: 5,977,433
[45] Date of Patent: *Nov. 2, 1999

[54] MAINTENANCE OF MALE-STERILE PLANTS

[75] Inventors: Mark Williams; Jan Leemans, both of Gent, Belgium

[73] Assignee: Plant Genetic Sysetms, N.V., Brussels, Belgium

[*] Notice: This patent is subject to a terminal disclaimer.

[21] Appl. No.: 09/025,583

[22] Filed: Feb. 18, 1998

Related U.S. Application Data

[62] Division of application No. 08/351,413, filed as application No. PCT/EP93/01489, Jun. 11, 1993, Pat. No. 5,750,867, which is a continuation of application No. 07/970,849, Nov. 3, 1992, abandoned, which is a continuation of application No. 07/899,072, Jun. 12, 1992, abandoned.

[51] Int. Cl.$^6$ .............................. A01H 5/00; A01H 1/02; C12N 15/29; C12N 15/82; C12N 15/55

[52] U.S. Cl. ..................... 800/274; 800/268; 800/275; 800/278; 800/287; 800/288; 800/298; 800/303; 800/320.1; 435/69.1; 435/199; 435/418; 435/419; 435/468; 536/23.2; 536/23.6; 536/23.7; 536/24.1; 536/24.5

[58] Field of Search .................... 47/58, DIG. 1; 435/69.1, 172.3, 199, 418, 419, 468; 536/23.2, 23.6, 23.7, 24.1, 24.5; 800/205, DIG. 56, 260, 268, 274, 275, 278, 287, 288, 298, 303, 320.1

[56] References Cited

U.S. PATENT DOCUMENTS

| | | | |
|---|---|---|---|
| 3,710,511 | 1/1973 | Patterson | 47/58 |
| 3,861,079 | 1/1975 | Patterson | 47/58 |
| 4,658,084 | 4/1987 | Beversdorf et al. | 800/200 |
| 4,727,219 | 2/1988 | Brar et al. | 800/200 |
| 5,356,799 | 10/1994 | Fabijanski et al. | 435/172.3 |
| 5,478,369 | 12/1995 | Albertsen et al. | 47/58 |

FOREIGN PATENT DOCUMENTS

| | | |
|---|---|---|
| 0344029A1 | 11/1989 | European Pat. Off. . |
| 0412911A1 | 2/1991 | European Pat. Off. . |
| WO 90/08828 A2 | 8/1990 | WIPO . |

OTHER PUBLICATIONS

Mariani et al., Nature, vol. 357, pp. 384–387 (Jun. 1992).
Hartley, J. Mol. Biol., vol. 202, pp. 913–915 (1988).
Aarts et al., Nature, vol. 363, pp. 715–717 (Jun. 1993).
Stoskopf et al., Plant Breeding Theory and Practice, Cell and Molecular Biology Tools for Plant Breeding, Chapter 22, pp. 453–472 (1993).
Zabaleta et al., Proc. Natl. Acad. Sci., USA, vol. 93, pp. 11259–11263 (Oct. 1996).
Poehlman, Breeding Field Crops, Third Edition, Hybrid Corn, pp. 473–476.
Sprague, Production of Hybrid Seed, American Society of Agronomy, Inc., pp. 685–693, (1977).
Mascarenhas, J. P. pp. 99–105 In: Mol. Basis Plant Dev., Goldberg, R., ed., Alan R. Liss, Inc.: New York, 1988.
Evans et al. Biochem. Soc. Trans. 20: 344S 1992.
Mazzolini et al. Plant Mol. Biol. 20: 715–731, 1992.
Sanders, P.G. Enzyme Microb–Technol. 9: 250–251, Apr. 1987.
Smith et al. Nature 334: 724–726, Aug. 1988.
Napoli et al. Plant Cell 2: 279–289, Apr. 1990.
Chaudhury, A. Plant Cell 6: 1277–1283, Oct. 1993.

*Primary Examiner*—David T. Fox
*Attorney, Agent, or Firm*—Birch, Stewart, Kolasch & Birch, LLP

[57] ABSTRACT

Transgenic plants that have, stably integrated into their nuclear genome, a maintainer gene comprising a fertility-restorer gene and a pollen-lethality gene. The plants can be used to maintain a homogenous population of male-sterile plants.

30 Claims, No Drawings

MAINTENANCE OF MALE-STERILE PLANTS

This application is a Rule 53(b) Divisional Application of U.S. application Ser. No. 08/351,413 filed on Feb. 8, 1995, now U.S. Pat. No. 5,750,867, which is a national phase application from PCT International Application Number PCT/EP93/01489 filed on Jun. 11, 1993 and claims priority thereon pursuant to 35 U.S.C. § 371, which is a continuation of U.S. application Ser. No. 07/970,849 filed Nov. 3, 1992, now Abandoned, which is a continuation of U.S. application Ser. No. 07/899,072 filed on Jun. 12, 1992, now Abandoned, the entire contents of each of which are incorporated by reference.

FIELD OF THE INVENTION

This invention relates to a process for maintaining male-sterile plant lines that can be used for the production of hybrid seed of a crop, to maintainer plants that can be used in such a process, and to maintainer genes that can be used to produce such maintainer plants.

BACKGROUND OF THE INVENTION

In many, if not most, plant species, the development of hybrid cultivars is highly desired because of their generally increased productivity due to heterosis: the superior performance of hybrid individuals compared with their parents (see, e.g., Fehr (1987) "Principles of Cultivar Development, Volume 1: Theory and Technique", MacMillan Publishing Company, New York; Allard (1960) "Principles of Plant Breeding", John Wiley and Sons, Inc., New York).

The development of hybrid cultivars of various plant species depends upon the capability to achieve almost complete cross-pollination between parents. This is most simply achieved by rendering one of the parent lines male-sterile (i.e., with pollen being absent or nonfunctional); for example, by manually removing the one parent's anthers or by providing the one parent with naturally occurring cytoplasmic or nuclear genes that prevent anther and/or pollen development and/or function, using classical breeding techniques (for a review of the genetics of male-sterility in plants, see Kaul (1988) "Male Sterility in Higher Plants", Springer Verlag, New York).

For hybrid plants where the seed is the harvested product (e.g., corn and oilseed rape), it is, in most cases, also necessary to ensure that fertility of the hybrid plants is fully restored. In plants in which the male-sterility is under genetic control, this requires the use of genes that can restore male-fertility. Hence, the development of hybrid cultivars is mainly dependent on the availability of suitable and effective sterility and restorer genes.

Endogenous nuclear loci are known for most plant species that contain genotypes which effect male-sterility, and generally, such loci need to be homozygous for particular recessive alleles in order to result in a male-sterile phenotype. The presence of a dominant male-fertile allele at such loci results in male-fertility.

Recently, it has been shown that male-sterility can be induced in a plant by providing the plant with a nuclear male-sterility genotype that includes a chimaeric male-sterility gene comprising a DNA sequence (or male-sterility DNA) coding, for example, for a cytotoxic product (such as an RNase) and under the control of a promoter which is predominantly active in selected tissue of the plant's male reproductive organs. In this regard, tapetum-specific promoters, such as the promoter of the TA29 gene of *Nicotiana tabacum*, have been shown to be particularly useful for this purpose (Mariani et al (1990) Nature 347:737; European patent publication ("EP") 0,344,029). By providing the nuclear genome of the plant with such a male-sterility gene, an artificial nuclear male-sterility locus is created containing the artificial male-sterility genotype that results in a male-sterile plant.

In addition, it has been recently shown that male-fertility can be restored to such a nuclear male-sterile plant with a chimaeric fertility-restorer gene comprising another DNA sequence (or fertility-restorer DNA) that codes, for example, for a protein that inhibits the activity of the cytotoxic product or otherwise prevents the cytotoxic product from being active at least in the selected tissue of the plant's male reproductive organs (EP 0,412,911). For example, the barnase gene of *Bacillus amyloliquefaciens* codes for an RNase (Barnase) which can be inhibited by a protein (Barstar) that is encoded by the barstar gene of *B. amyloliquefaciens*. Hence, the barnase gene can be used for the construction of a chimaeric male-sterility gene while the barstar gene can be used for the construction of a chimaeric fertility-restorer gene. Experiments in different plant species (e.g., oilseed rape) have shown that such a chimaeric barstar gene can fully restore the male-fertility of male-sterile lines in which the male-sterility was due to the presence of a chimaeric barnase gene (EP 0,412,911: Mariani et al (1991) Proceedings of the CCIRC Rapeseed Congress, Jul. 9–11, 1991 Saskatoon, Saskatchewan, Canada; Mariani et al (1992) Nature 357:384). By coupling a marker gene, such as a dominant herbicide resistance gene (for example, the bar gene coding for phosphinothricin acetyl transferase (PAT) that converts herbicidal phosphinothricin to a non-toxic compound [De Block et al (1987) EMBO J. 6:2513]), to the chimaeric male-sterility and/or fertility restorer gene, breeding systems can be implemented to select for uniform populations of male-sterile plants (EP 0,344,029; EP 0,412,911).

The production of hybrid seed of any particular cultivar of a plant species requires the: 1) maintenance of small quantities of pure seed of each inbred parent; and 2) the preparation of larger quantities of seed of each inbred parent. Such larger quantities of seed would normally be obtained by several (usually two) seed-multiplication rounds, starting from a small quantity of pure seed ("basic seed") and leading, in each multiplication round, to a larger quantity of seed of the inbred parent and finally to a stock of seed of the inbred parent ("parent seed" or "foundation seed") which is of sufficient quantity to be planted to produce the desired quantities of hybrid seed. Of course, in each seed-multiplication round, larger planting areas (fields) are required.

In order to maintain and enlarge a small stock of seeds of male-sterile plants, it has been necessary to cross the parent male-sterile plants with normal pollen-producing parent plants. The offspring of such a cross will, in all cases, be a mixture of male-sterile and male-fertile plants, and the latter have to be removed from the former. With male-sterile plants containing an artificial male-sterility locus as described above, such removal can be facilitated by genetically linking the chimaeric male-sterility gene to a suitable marker gene, such as the bar gene, which allows the easy identification and removal of the male-fertile plants. EP 0,198,288 and U.S. Pat. No. 4,717,219, by comparison, describe methods for linking such marker genes (which can be visible markers or dominant conditional markers) to endogenous nuclear loci containing male-sterility genotypes.

However, even when suitable marker genes are linked to male-sterility genotypes, the maintenance of parent male-sterile plants still requires the removal from the field of a substantial number of plants. For instance, in systems using a herbicide resistance gene (e.g., the bar gene) linked to a chimaeric male-sterility gene, only half of the parent stock will result in male-sterile plants, thus requiring the removal of the male-fertile plants by herbicide spraying prior to flowering. In any given field, the removal of male-fertile plants effectively reduces the potential yield of hybrid seed or the potential yield of male-sterile plants during each round of seed multiplication for producing of parent seed. This is economically unattractive for many important crop species such as corn and oilseed rape. In order to minimize the number of male-fertile plants which have to be removed, male-fertile maintainer plants have been sought which, when crossed with a male-sterile parent plant, produce a minimum, preferably no, male-fertile offspring, thereby minimizing or avoiding altogether the need to remove such male-fertile offspring. To solve an analogous problem, U.S. Pat. Nos. 3,710,511 and 3,861,079 have described procedures for producing and maintaining a homogenous population of male-sterile plants by using specific chromosomal abnormalities that are differentially transmitted to the egg and the sperm in the plants.

SUMMARY OF THE INVENTION

In accordance with this invention, a cell of a transgenic plant ("the maintainer plant") is provided, in which the nuclear genome contains stably integrated therein: 1) at a first locus or male-sterility locus, a male-sterility genotype in homozygous condition; and 2) at a second locus or maintainer locus, a maintainer gene in heterozygous condition; the male-sterility locus and the maintainer locus preferably being unlinked; the maintainer gene being a foreign DNA sequence, preferably a foreign chimaeric DNA sequence, containing:
  a) a fertility-restorer gene that comprises at least:
    i) a fertility-restorer DNA encoding a restorer RNA and/or protein or polypeptide which, when produced or overproduced in some or all of the cells, preferably stamen cells, of the plant, prevents phenotypic expression of the nuclear male-sterility genotype that would render the plant male-sterile in the absence of expression of the fertility-restorer DNA in the some or all stamen cells; and
    ii) a restorer promoter capable of directing expression of the fertility-restorer DNA at least in some or all of the cells, preferably stamen cells, of the plant, so that the phenotypic expression of the nuclear male-sterility genotype is prevented, the fertility-restorer DNA being in the same transcriptional unit as, and under the control of, the restorer promoter and
  b) a pollen-lethality gene that is selectively expressed in microspores and/or pollen of the plant to produce nonfunctional pollen and that comprises at least:
    iii) a pollen-lethality DNA coding for a pollen-lethality RNA and/or protein or polypeptide that, when produced or overproduced in the microspores and/or pollen, significantly disrupts their metabolism, functioning and/or development; and
    iv) a pollen-specific promoter capable of directing expression of the pollen-lethality DNA selectively in the microspores and/or pollen of the plant, the pollen-lethality DNA being in the same transcriptional unit as, and under the control of, the pollen specific promoter.

The cell of the maintainer plant of this invention preferably also comprises, especially in the maintainer locus, at least one first marker gene which comprises at least:
  v) a first marker DNA encoding a first marker RNA and/or protein or polypeptide which, when present at least in a first specific tissue or specific cells of the plant, renders the plant easily separable from other plants which do not contain the first marker RNA, protein or polypeptide encoded by the first marker DNA at least in the first specific tissue or specific cells; and
  vi) a first marker promoter capable of directing expression of the first marker DNA at least in the first specific tissue or specific cells, the first marker DNA being in the same transcriptional unit as, and under the control of, the first marker promoter.

The male-sterility genotype in the cell of the maintainer plant of this invention can be foreign or endogenous but is preferably a foreign, especially chimaeric, male-sterility gene which comprises:
  1) a male-sterility DNA encoding a sterility RNA and/or protein or polypeptide which, when produced or overproduced in a stamen cell of the plant in the absence of the restorer RNA, protein or polypeptide, significantly disturbs the metabolism, functioning and/or development of the stamen cell; and
  2) a sterility promoter capable of directing expression of the male-sterility DNA selectively in stamen cells of the plant, the male-sterility DNA being in the same transcriptional unit as, and under the control of, the sterility promoter.

The male-sterility genotype in the maintainer plant cell of this invention preferably comprises, especially in the male-sterility locus, at least one second marker gene which comprises at least:
  3) a second marker DNA encoding a second marker RNA and/or protein or polypeptide which, when present at least in the second specific tissue or specific cells of the plant, renders the plant easily separable from other plants which do not contain the second marker RNA, protein or polypeptide encoded by the second marker DNA at least in the second specific tissue or specific cells; and
  4) a second marker promoter capable of directing expression of the second marker DNA at least in the second specific tissue or specific cells, the second marker DNA being in the same transcriptional unit as, and under the control of, the second marker promoter.

Also in accordance with this invention are provided maintainer plants, the seeds of such plants, and plant cell cultures, all of which consist essentially of the cells of this invention.

Further in accordance with this invention are provided the maintainer gene and plasmids containing the maintainer gene, as well as bacterial host cells (e.g., *E. coli* or Agrobacterium) containing such plasmids.

Still further in accordance with this invention is provided a process for producing, preferably enlarging, a homogeneous population of male-sterile plants and their seed that contain a nuclear male-sterility gene in homozygous condition, the process comprising the step of crossing the male-sterile plants with the maintainer plants of this invention. The seed from the resulting male-sterile plants can be harvested and grown into the male-sterile plants. Hybrid seed can then be produced by crossing the male-sterile plants with male-fertile plants of another inbred parent line used as pollinators.

Yet further in accordance with this invention is provided a process for producing, preferably enlarging, a population of the maintainer plants, comprising the step of selfing the maintainer plants.

BRIEF DESCRIPTION OF THE TABLE

Table 1 describes a ten step procedure to obtain corn (e.g., H99) maintainer plants according to the present invention.

DETAILED DESCRIPTION OF THE INVENTION

A male-sterile plant of this invention is a plant of a given species with a nuclear male-sterility genotype.

A restorer plant of this invention is a plant of the same plant species containing, within its nuclear genome, a fertility-restorer gene that is able to restore the male-fertility in offspring which are obtained from a cross between the male-sterile plant and the restorer plant and which contain both the male-sterility genotype and the fertility-restorer gene.

A restored plant of this invention is a plant of the same species that is male-fertile and that contains, within its nuclear genome, the male-sterility genotype and the fertility-restorer gene.

A parent plant or parent of this invention is a plant that can be used for the production of hybrid seed. The female or seed parent plant is the parent from which the hybrid seed is harvested. For the purposes of this invention, the female parent will always be a male-sterile plant. The male or pollen parent is the parent that is used to fertilize the female parent. In many cases, the male parent will also be a restorer plant.

A line is the progeny of a given individual plant.

The male-sterility genotype of this invention is the genotype of at least one locus, preferably only one locus, in the nuclear genome of a plant (i.e., the male-sterility locus), the allelic composition of which can result in male-sterility in the plant. A male-sterility genotype can be endogenous to the plant, but it is generally preferred that it be foreign to the plant. Preferred foreign male-sterility genotypes are those in which the allele responsible for male-sterility contains a foreign male-sterility gene that comprises:

1) a male-sterility DNA encoding a sterility RNA and/or protein or polypeptide which, when produced or overproduced in a stamen cell of the plant, significantly disturbs the metabolism, functioning and/or development of the stamen cell; and 2) a sterility promoter capable of directing expression of the male-sterility DNA selectively in stamen cells of the plant, the male-sterility DNA being in the same transcriptional unit as, and under the control of, the sterility promoter.

Such a male-sterility gene is always a dominant allele at a foreign male-sterility locus. The recessive allele corresponds to the absence of the male-sterility gene in the nuclear genome of the plant.

Preferred foreign male-sterility DNAs and sterility promoters that can be used in the male-sterility genes in female parent plants and maintainer plants of this invention have been described in EP 0,344,029. A particularly useful male-sterility DNA codes for Barnase (Hartley (1988) J. Mol. Biol. 202:913). Particularly useful sterility promoters are tapetum-specific promoters such as the promoter of the TA29 gene of *Nicotiana tabacum* (EP 0,344,029) which can be used in tobacco, oilseed rape, lettuce, chicory, corn and other plant species; the PT72, the PT42 and PE1 promoters from rice, the sequences of which are given in SEQ ID no. 7, SEQ ID no. 8, and SEQ ID no. 9, respectively, in the Sequence Listing and which can be used in rice and other plant species (PCT application PCT/EP 92/00274); and the PCA55 promoter from corn, the sequence of which is given in SEQ ID No. 10, which can be used in corn and other plant species (PCT application PCT/EP 92/00275).

A preferred endogenous male-sterility genotype is one in which a recessive allele ("m") in homozygous condition (m/m) at a male-sterility locus produces male-sterility. At a male-sterility locus, male-fertility would otherwise be encoded by a corresponding dominant allele ("M"). Such a male-sterility genotype is known in many plant species (see Kaul (1988) supra; and 1992 issues of Maize Genetics Cooperation Newsletter, published by the Department of Agronomy and U.S. Department of Agriculture, University Of Missouri, Columbia, Mo., U.S.A.). The DNA sequences in the nuclear genome of a plant corresponding to m and M alleles can be identified by gene tagging, i.e., by insertional mutagenesis using transposons, or by means of T-DNA integration (see, e.g., Wienand and Saedler (1987) In "Plant DNA Infectious Agents", Ed. by T. H. Hohn and J. Schell, Springer Verlag, New York, p. 205; Shepherd (1988) In "Plant Molecular Biology: a Practical Approach", IRL Press, p. 187; and Teeri et al (1986) EMBO J. 5:1755).

Fertility-restorer DNAs and restorer promoters that can be used in the maintainer genes of this invention with a foreign male-sterility genotype have been described in EP 0,412,911. In this regard, fertility-restorer genes in which the fertility-restorer DNA encodes Barstar (Hartley (1988) J. Mol. Biol. 202:913) and is under control of tapetum-specific promoters, such as those described above as sterility promoters, are of particular use. In particular, it is believed that a fertility-restorer DNA coding for a mutant of Barstar, in which the cysteine residue at its position 40 is replaced by serine (Hartley (1989) TIBS 14:450), functions better in restoring the fertility in the restored plants of some species.

When an endogenous male-sterility genotype is homozygous for a recessive allele m, it is preferred that the fertility-restorer gene be the dominant allele M of that male-sterility genotype, preferably under the control of its own promoter. The DNA corresponding to such a dominant allele, including its natural promoter, can be isolated from the nuclear genome of the plant by means of gene tagging, as described above.

The pollen-lethality DNAs that are used in the pollen-lethality genes of this invention preferably encode an RNA and/or a protein or polypeptide that, when expressed in microspores or pollen, significantly disrupts their metabolism, functioning and/or development. In this regard, the pollen-lethality DNAs can encode RNAs, proteins or polypeptides such as those are encoded by the male-sterility DNAs described in EP 0,344,029. Of particular interest are male-sterility DNAs that encode ribonucleases (EP 0,344,029) such as RNase T1 from *Asperqillus oryzae* (Quaas et al (1988) Eur. J. Biochem. 173:617) or Barnase from *Bacillus amyloliquefaciens* (Hartley (1988) J.Mol.Biol. 202:913).

So that the pollen-lethality DNA is expressed selectively in microspores or pollen of the maintainer plant, it is preferred that the pollen-specific promoter, which controls the pollen-lethality DNA in the pollen-lethality gene, be a promoter capable of directing gene expression selectively in the microspores and/or pollen of the plant. Such a pollen-specific promoter can be an endogeneous promoter or a foreign promoter and can be from the nuclear genome or from the mitochondrial or chloroplast genome of a plant cell. But in any event, the pollen-specific promoter is foreign in the nuclear genome of the plant being transformed. Preferably the pollen-specific promoter causes the pollen-lethality DNA to be expressed only in the microspores and/or pollen, i.e., after meiosis of the microsporocytes in the anthers. The pollen-specific promoter can be selected and isolated in a well known manner from a plant species, preferably the plant species to be rendered male-sterile, so that the pollen-specific promoter directs expression of the pollen-lethality DNA selectively in the microspores and/or pollen so as to kill or disable the microspores and/or pollen in which the pollen-lethality gene is expressed. The pollen-specific promoter is preferably also selected and isolated so that it is effective in preventing expression of the pollen-lethality DNA in other tissues of the plant. For example, a suitable endogeneous pollen-specific promoter can be identified and isolated in a plant, to be rendered male-sterile, by 1. searching for an mRNA which is only present in the plant during the development of its microspores and/or pollen;
2. optionally isolating the microspore- and/or pollen-specific mRNA;
3. preparing and isolating a cDNA from the microspore- and/or pollen-specific mRNA;
4. using this cDNA as a probe to identify regions in the plant genome which contain DNA coding for the corresponding microspore- and/or pollen-specific DNA or alternatively using inverse polymerase chain reactions for the geometric amplification of the DNA sequences which flank, upstream and downstream, a chosen core region of the genomic DNA corresponding to the sequence of the microspore- and/or pollen-specific cDNA; and
5. identifying the portion of the plant genome that is upstream (i.e., 5') from the DNA coding for the microspore- and/or pollen-specific mRNA and that contains the promoter of this DNA.

Examples of such pollen-specific promoters are well known (see, MacCormick (1991) TIG 7:298). In this regard, Hamilton et al (1989) Sex. Plant Reprod. 2:208 describes a pollen-specific clone ("Zmg13") from maize inbred line W-22, and the use of the promoter sequences of the clone to direct pollen-specific expression in tobacco has been described by Guerrero et al (1990) Mol. Gen, Genet. 224:161). Other pollen-specific promoters that are likewise believed to be useful are the promoter of the gene corresponding to the *Nicotiana tabacum* pollen-specific cDNA NTPc303 described by Weterings et al (1992) Plant Mol. Biol. 18:1101; and the promoter of the gene corresponding to the *Brassica napus* pollen-specific cDNA B54 described by Shen and Hsu (1992) Mol. Gen. Genet. 234:379.

If the fertility-restorer DNA in the fertility-restorer gene of the maintainer gene is also expressed in microspores and/or pollen at the same time as the pollen-lethality DNA is expressed (due, for instance, to the activity of the restorer promoter in microspores and/or pollen), it is preferred that the pollen-lethality DNA be different from the male-sterility DNA (the expression of which is intended to be prevented by expression of the fertility-restorer DNA of the maintainer gene). For example, if the male-sterility DNA encodes Barnase in the male-sterile plants to be maintained, the fertility-restorer DNA in the maintainer gene should encode Barstar. Thus, if the restorer promoter in the maintainer gene also directs expression of the fertility-restorer DNA in microspores and/or pollen and at the same time as the pollen-lethality DNA is expressed, the pollen-lethality DNA preferably should not encode Barnase but rather, for example, another RNAse such as RNAse T1.

First and second marker DNAs and first and second marker promoters that can be used in the first and second marker genes of this invention are also well known (EP 0,344,029; EP 0,412,911). In this regard, it is preferred that the first and second marker DNAs be different, although the first and second marker promoters may be the same.

The fertility-restorer gene, the male-sterility gene, the pollen-lethality gene, and the first and second marker genes in accordance with this invention are generally foreign DNA sequences, preferably foreign chimaeric DNA sequences. Such foreign DNA sequences are preferably provided with suitable 3' transcription regulation sequences and polyadenylation signals, downstream (i.e., 3') from their respective fertility-restorer DNA, male-sterility DNA, pollen-lethality DNA, and first and second marker DNAs. In this regard, either foreign or endogenous, transcription termination and polyadenylation signals suitable for obtaining expression of such DNA sequences can be used. For example, the foreign 3' untranslated ends of genes, such as gene 7 (Velten and Schell (1985) Nucl. Acids Res. 12:6998), the octopine synthase gene (De Greve et al (1982) J.Mol. Appl. Genet. 1:499; Gielen et al (1983) EMBO J. 3:835; and Ingelbrecht et al (1989) The Plant Cell 1:671), the nopaline synthase gene of the T-DNA region of *Agrobacterium tumefaciens* Ti-plasmid (De Picker et al (1982) J.Mol. Appl. Genet. 1:561), the chalcone synthase gene (Sommer and Saedler (1986) Mol. Gen. Genet. 202: 429–434), and the CaMV 19S/35S transcription unit (Mogen et al (1990) The Plant Cell 2:1261–1272), can be used.

By "foreign" with regard to a gene or genotype of this invention is meant that the gene or genotype contains a foreign DNA sequence such as a male-sterility DNA, a fertility-restorer DNA, a pollen-lethality DNA, or a marker DNA and/or a foreign promoter such as a sterility promoter, a restorer promoter, a pollen-specific promoter or a marker promoter. By "foreign" with regard to any DNA sequence, such as a coding sequence or a promoter, in a gene or genotype of this invention is meant that such a DNA is not in the same genomic environment in a plant cell, transformed with such a DNA in accordance with this invention, as is such a DNA when it is naturally found in the cell of the plant, bacteria, animal, fungus, virus or the like, from which such a DNA originates. This means, for example, that a foreign fertility-restorer DNA, male-sterility DNA, pollen-lethality DNA, or marker DNA can be: 1) a nuclear DNA in a plant of origin; 2) endogenous to the transformed plant cell (i.e., from a plant of origin with the same genotype as the plant being transformed); and 3) within the same transcriptional unit as its own endogenous promoter and 3' end transcription regulation signals (from the plant of origin) in the foreign gene or genotype in the transformed plant cell; but 4) inserted in a different place in the nuclear genome of the transformed plant cell than it was in the plant of origin so that it is not surrounded in the transformed plant cell by the genes which surrounded it naturally in the plant of origin. Likewise, a foreign fertility-restorer DNA, male-sterility DNA, pollen-lethality DNA, or marker DNA can also, for example, be: 1) a nuclear DNA in a plant of origin; and 2) endogenous to the transformed plant cell; but 3) in the same transcriptional unit as a different (i.e., not its own) endogenous promoter and/or 3' end transcription regulation signals in a foreign chimaeric gene or genotype of this invention in a transformed plant cell. A foreign fertility-restorer DNA, male-sterility DNA, pollen-lethality DNA, or marker DNA can also, for example, be: 1) a nuclear DNA in a plant of origin; and 2) endogenous to the transformed plant cell; but 3) in the same transcriptional unit as a heterologous promoter and/or 3' end transcription regulation signals in a foreign chimaeric gene or genotype of this invention in a transformed plant cell. A foreign fertility-restorer DNA, a male-sterility DNA, pollen-lethality DNA, or marker DNA can also, for example, be heterologous to the transformed plant cell and in the same transcriptional unit as an endogenous promoter and/or 3' transcription regulation signals (e.g., from the nuclear genome of a plant with the same genotype as the plant being transformed) in a foreign chimaeric DNA sequence of this invention in a transformed plant cell. Preferably, each fertility-restorer DNA, male-sterility DNA, pollen-lethality DNA, and marker DNA of this invention is heterologous to the plant cell being transformed.

By "heterologous" with regard to a DNA, such as a fertility-restorer DNA, a male-sterility DNA, a pollen-lethality DNA, a marker DNA, a fertility-restorer promoter, a sterility promoter, a pollen-specific promoter or a marker promoter or any other DNA sequence in a gene or a genotype of this invention is meant that such a DNA is not naturally found in the nuclear genome of cells of a plant with the same genotype as the plant being transformed. Examples of heterologous DNAs include chloroplast and mitochondrial DNAs obtained from a plant with the same genotype as the plant being transformed, but preferred examples are chloroplast, mitochondrial, and nuclear DNAs from plants having a different genotype than the plant being transformed, DNAs from animal and bacterial genomes, and chromosomal and plasmidial DNAs from fungal, bacterial and viral genomes.

By "chimaeric" with regard to a foreign DNA sequence of this invention is meant that at least one of its coding sequences : 1) is not naturally found under the control of the promoter present in the foreign DNA sequence; and/or 2) is not naturally found in the same genetic locus as at least one of its associated marker DNAs. Examples of foreign chimaeric DNA sequences of this invention comprise a pollen-lethality DNA of bacterial origin under the control of a pollen-specific promoter of plant origin; and a pollen-lethality DNA of plant origin under the control of a pollen-specific promoter of plant origin and in the same genetic locus as a marker DNA of bacterial origin.

By "endogenous" with respect to a gene or genotype of this invention is meant that it is not foreign.

The foreign genes and genotypes of this invention, such as the male-sterility gene and genotype, the fertility-restorer gene and the pollen-lethality gene, can be described like any other genotype: capital letters denote the presence of the foreign genes and genotypes (the dominant allele) while small letters denote their absence (the recessive allele). Hence, in this description of the invention, "S" and "s" will denote the respective presence and absence of the male-sterility gene, "R" and "r" will denote the respective presence and absence of the fertility-restorer gene, and "P" and "p" will denote the respective presence and absence of the maintainer gene.

For an endogeneous male-sterility genotype of this invention, "m" will denote the recessive allele, and "M" will denote the dominant allele. Thus, the recessive allele m in homozygous condition (m/m) at a male-sterility locus would result in male-sterility, and the dominant allele M, when present at a male-sterility locus either in homozygous or heterozygous condition, results in male-fertility.

The cell of a plant, particularly a plant capable of being infected with Agrobacterium such as most dicotyledonous plants (e.g., *Brassica napus*), can be transformed using a vector that is a disarmed Ti-plasmid containing the male-sterility gene and/or the fertility-restorer gene and/or the pollen-lethality gene and/or the maintainer gene and/or the marker gene(s) of this invention and carried by Agrobacterium. This transformation can be carried out using the procedures described, for example, in EP 0,116,718 and EP 0,270,822. Preferred Ti-plasmid vectors contain a foreign DNA sequence of this invention between the border sequences, or at least located to the left of the right border sequence, of the T-DNA of the Ti-plasmid. Of course, other types of vectors can be used to transform the plant cell, using procedures such as direct gene transfer (as described, for example, in EP 0, 233,247), pollen mediated transformation (as described, for example, in EP 0,270,356, PCT publication WO 85/01856, and U.S. Pat. No. 4,684,611), plant RNA virus-mediated transformation (as described, for example, in EP 0,067,553 and U.S. Pat. No. 4,407,956) and liposome-mediated transformation (as described, for example, in U.S. Pat. No. 4,536,475). Cells of monocotyledonous plants, such as the major cereals including corn, rice, wheat, barley and rye, can be transformed as described in PCT application PCT/EP 91/02198. In case the plant to be transformed is corn, other recently developed methods can also be used such as, for example, the methods described for certain lines of corn by Fromm et al (1990) Bio/Technology 8:833, Gordon-Kamm et al (1990) Bio/Technology 2:603 and Gould et al (1991) Plant Physiol. 95:426. In case the plant to be transformed is rice, recently developed methods can also be used such as, for example, the method described for certain lines of rice by Shimamoto et al (1989) Nature 338:274; Datta et al (1990) Bio/Technology 8:736; and Hayashimoto et al (1990) Plant Physiol. 93:857.

The so-transformed cell can be regenerated into a mature plant, and the resulting transformed plant can be used in a conventional breeding scheme to produce more transformed plants with the same characteristics or to introduce the male-sterility gene, the fertility-restorer gene, the pollen-lethality gene, the marker genes and/or the maintainer gene of this invention in other varieties of the same or related plant species. Seeds obtained from such plants contain the gene(s) of this invention as a stable genomic insert.

The maintainer plant of this invention is of the same species as a male-sterile plant line and can be used for the maintenance of the male-sterile line, i.e., to maintain a homogeneous population of male-sterile plants and a stock of pure seed of the female parent. The maintainer plant of this invention is itself a plant in which male-fertility has been restored and the genome of which contains both a male-sterility genotype and, in the maintainer locus, a fertility-restorer gene of this invention.

If a plant line with a homozygous male-sterility genotype ($A^{m/m}$ or $A^{S/S}$) is available, a maintainer plant for the male-sterile line can be directly obtained by transforming a male-sterile plant of the line with the maintainer gene of this invention and then selecting those transgenic plants which are male-fertility restored plants and in which the maintainer gene is stably integrated in the nuclear genome so that the genetic locus of the male-sterility genotype and of the maintainer gene are unlinked and segregate independently.

If the male-sterility genotype is foreign to the plant line, alternative strategies can be followed. For example, the maintainer plant of the present invention can be obtained by transforming a plant cell of the plant line (A) with the maintainer gene of this invention (P); and then regenerating, from the so-transformed plant cell, a transgenic plant containing, stably integrated in its genome, the maintainer gene. Such a transgenic plant ($A^{P/p}$) can then be crossed as a female parent with a plant $A^{S/s,R/r}$ of the same line, which contains at separate loci in its genome a male-sterility gene (S) and a corresponding fertility-restorer gene (R), both in heterozygous condition, but which lacks the maintainer gene. Thus, the cross is in fact: $A^{S/s,R/r,P/p}$ (male)×$A^{s/s,r/r/P/p}$ (female), and the offspring with the genotype $A^{S/s,r/r/P/p}$ (or hereinafter "$A^{S/s,P/p}$" for convenience) are selected and selfed. One eighth of the offspring that have the desired genotype ($A^{S/S,P/P}$) for a maintainer plant of this invention can then be selected. Another eighth of the offspring with the genotype ($A^{S/S,P/p}$) can be used as male-sterile plants to be maintained.

Isolation of plants with desired genotypes can be achieved by means of conventional testcrosses (see, e.g., Fehr (1987) supra), preferably supplemented by detection of the presence of specific genes at the DNA level, e.g., by means of amplification of DNA fragments by the polymerase chain reaction, by Southern blot analysis and/or by phenotypic analysis for the presence and expression of first or second marker genes of this invention.

The cross of a male-sterile plant containing a male-sterility genotype in homozygous condition ($A^{S/S}$ or $A^{m/m}$) with a maintainer plant of this invention ($A^{S/S,P/p}$ or $A^{m/m,P/p}$, respectively) results in a population of seeds that all contain the male-sterility genotype in homozygous condition ($A^{S/S}$ or $A^{m/m}$, respectively) because the maintainer gene is not transmitted through the pollen. This property can be used to advantage in maintaining the basic seed and in the multiplication of basic seed for the final production of parent seed.

The maintainer plants of this invention ($A^{S/S,P/p}$ or $A^{m/m,P/p}$) can themselves be maintained by selfing. The offspring of such selfing will consist of 50% male-fertile maintainer plants ($A^{S/S,P/p}$ or $A^{m/m,P/p}$, respectively) and 50% male-sterile plants containing the male-sterility genotype in homozygous condition ($A^{S/S}$ or $A^{m/m}$, respectively). If desired, the male-sterile plants can be removed either manually on the basis of the male-sterile phenotype or, if the maintainer gene comprises a suitable first marker gene, preferably a first marker gene whose expression confers herbicide resistance to the plant, by using the phenotypic expression of the first marker gene (e.g, by applying herbicide to the offspring so that male-sterile plants that lack the herbicide-resistance gene are killed while maintainer plants with the herbicide-resistance gene survive).

Thus, the maintainer plant of this invention can be easily used to maintain a homogeneous population of male-sterile plants. In this regard, basic seed of a female parent of a given plant species can be crossed with an appropriate male parent to produce hybrid seed. Also, the maintainer plant of this invention can be used economically to multiply the basic seed of a female parent of a given plant species, so as to obtain sufficient quantities of female parent seed that can be crossed with an appropriate male parent to produce desired quantities of hybrid seed.

A male-sterile line, that is maintained and multiplied by the use of the maintainer plants of this invention, can be used for the production of hybrid seed. In principle, the male-sterile line ($A^{S/S}$) can be crossed directly with another male parent line ($B^{s/s}$) to produce hybrid seed ($AB^{S/s}$). However, since all hybrid plants are male-sterile, no reproduction and no seed set will occur. This is not a problem if the seed is not the harvested product (e.g., with lettuce), but where seed is the harvested product (e.g., with corn and oilseed rape), male-fertility in the hybrid plants should be at least partially restored. This can be accomplished by crossing the male-sterile line with a male-fertile parent line (e.g., $B^{R/R}$) that is also a restorer line, i.e., that also contains a fertility-restorer gene (R). The hybrids produced ($AB^{S/s,R/r}$) will be fully male-fertile. Alternatively the male-sterile-line ($A^{S/S}$) can first be crossed with the male-fertile line ($A^{s/s}$) just prior to hybrid seed production. This has the advantage of giving a further multiplication of the female parent line. The offspring ($A^{S/s}$) can then be crossed with a suitable male-fertile parent line ($B^{s/s,r/r}$) to produce hybrid seed that is 50% male-fertile. If hybrid seed with 100% male fertility is desired, the offspring can be crossed with a suitable restorer male parent line ($B^{S/s,R/R}$).

In the case of a male-sterile line in which male-sterility is due to an endogenous male-sterility genotype ($A^{m/m}$) at a male-sterility locus, hybrid seed can easily be produced by crossing the male-sterile line ($A^{m/m}$) with a line that is homozygous with respect to the endogenous dominant (male-fertility) allele at that male-sterility locus ($B^{M/M}$). All hybrid offspring of this cross will have the genotype $AB^{M/m}$ and will be fertile.

The maintainer plants of this invention can also be used as pollinator (i.e., male-fertile) plants in a cross with wild-type plants ($A^{s/s,P/P}$) of the same inbred line. The progeny of this cross will all be male-sterile and heterozygous for the male-sterility genotype ($A^{S/s,P/p}$). The progeny can therefore be used directly for hybrid seed production by crossing with a pollinator plant line B ($B^{s/s,P/P}$). This scheme only requires a male-sterilization of the wild-type plants, for example by manually removing the anthers (e.g., in corn) or by using a male gametocide.

Of course, by using the maintainer plants of this invention to maintain a homogeneous population of plants that are homozygous with respect to a male-sterility allele (whether dominant or recessive) that is encoded in the nuclear genome, the maintainer plants acquire many of the characteristics of plants of a cytoplasmic male-sterile line. However, such plants do not have one of the major disadvantages of cytoplasmic male-sterile plants, namely the cytoplasmic uniformity of the various male-sterile lines which, in corn, has led to serious problems (see Craig (1977) In "Corn and Corn Improvement", G. F. Sprague, ed., American Society of Agronomy, Inc., Publisher, p. 671).

Thus, the maintainer gene of this invention, when introduced into a particular line of a plant species, can always be introduced into any other line by backcrossing, but since the maintainer gene can only be transmitted through an egg, it will always be associated with the cytoplasm of the line in which it was initially introduced. However, since a maintainer plant line is only used for maintenance of a male-sterile line and not as a female parent for hybrid seed production, the hybrid seed will always contain the cytoplasm of the female parent, as desired.

The following Examples illustrate this invention. Unless otherwise indicated, all experimental procedures for manipulating recombinant DNA were carried out by the standardized procedures described in Sambrook et al (1989) "Molecular Cloning: A Laboratory Manual, Second Edition", Cold Spring Harbor Laboratory Press, New York U.S.A. All polymerase chain reactions ("PCR") were performed under conventional conditions, using the Vent™ polymerase (Cat. No. 254L - Biolabs New England, Beverley, Mass. 01915, U.S.A.) isolated from *Thermococcus litoralis* (Neuner et al (1990) Arch. Microbiol. 153:205–207). Oligonucleotides were designed by the methods described by Kramer and Fritz (1968) Methods in Enzymology 154:350 and synthesized by the phosphoramidite method (Beaucage and Caruthers (1981) Tetrahedron Letters 22:1859) on an applied Biosystems 380A DNA synthesizer (Applied Biosystems B.V., Maarssen, Netherlands).

The following bacterial strains and plasmids, used in the Examples, are available from the Deutsche Sammlung für Mikroorganismen und Zellkulturen ("DSM"), Mascheroder Weg 1B, Braunschweig, Germany:

| Bacterial strain | plasmid | DSM No | Date of Deposit |
|---|---|---|---|
| E. coli WK6 | pMa5-8 | DSM 4567 | May 3, 1968 |
| E. coli WK6 | pMc5-8 | DSM 4566 | May 3, 1988 |

In the Examples, reference will be made to the following Sequence Listing:

| Sequence Listing | |
|---|---|
| SEQ ID no. 1 | genomic DNA comprising the promoter of the Zm13 gene from Zea mays |
| SEQ ID no. 2 | sequence of plasmid "pVE144" |
| SEQ ID no. 3 | sequence of plasmid "pVE108" |
| SEQ ID no. 4 | sequence of oligonucleotide "MDB80" |
| SEQ ID no. 5 | sequence of oligonucleotide "MDB81" |
| SEQ ID no. 6 | sequence of oligonucleotide "MDB82" |
| SEQ ID No. 7 | genomic DNA comprising the anther specific promoter "PT72" from rice |
| SEQ ID No. 8 | genomic DNA comprising the anther specific promoter "PT42" from rice |
| SEQ ID No. 9 | genomic DNA comprising the anther specific promoter "PE1" from rice |
| SEQ ID No. 10 | genomic DNA comprising the anther specific promoter "PCA55" from corn |
| SEQ ID No. 11 | Oligonucleotide Zm13OLI2 |
| SEQ ID No. 12 | Oligonucleotide Zm13OLI1 |
| SEQ ID No. 13 | Oligonucleotide Zm13OLI5 |
| SEQ ID No. 14 | Oligonucleotide BXOL2 |
| SEQ ID No. 15 | Oligonucleotide TA29SBXOL2 |
| SEQ ID No. 16 | Oligonucleotide PTA29OL5 |
| SEQ ID No. 17 | EcoRI-HindIII fragment of pTS218 carrying the maintainer gene. |

EXAMPLES

Example 1
Isolation of the Pollen-specific Promoter of the Zm13 Gene from Maize

A pollen-specific cDNA from Zea mays inbred line W-22, designated as "Zmc13", has been isolated and characterized by Hanson et al (1989) The Plant Cell 1:173. The corresponding genomic clone, designated as "Zmg13", containing substantial portions of the 5' flanking region has been isolated and characterized by Hamilton et al (1989) Sex. Plant Reprod. 2:208 (see also Hamilton et al (1992) Plant Mol. Biol. 18:211). The complete sequence of Zmg13 is shown in SEQ ID no. 1, and its promoter region will hereinafter be referred to as the "Zmg13 promoter".

A corresponding promoter region from corn inbred line H99 was isolated as follows. Genomic DNA of inbred line H99 was prepared as described by Dellaporta et al (1983) Plant Mol. Biol. Reports 1:19–21. Using the genome as a substrate, a 1471 bp fragment was amplified by PCR using the oligonucleotides MDB80 and MDB82, the sequences of which are shown in SEQ ID no. 4 and SEQ ID no. 6, respectively. MDB80 corresponds to nucleotides 8 to 28 of Zmg13, while MDB82 is complementary to nucleotides 1458 to 1478 of Zmg13. Then, the purified amplified 1471 bp fragment was used as a substrate for the amplification by PCR of a 1422 bp fragment, using the oligonucleotides MDB80 and MDB81. MDB81 is complementary to nucleotides 1409 to 1429 of Zmg13, and its sequence is shown in SEQ ID no. 5. By using MDB81, a NcoI site is created in the amplified 1422 bp fragment at the ATG translation initiation codon.

The 1422 bp fragment is then ligated in an SmaI site of pGEM2 (Promega Corporation, Madison, Wis. 53711, U.S.A.), yielding plasmid pMDB13, and the fragment is sequenced (Maxam and Gilbert (1980) Meth. Enzymol. 65:499). The pollen-specific promoter of the Zm13 gene of corn inbred line H99 is obtained from pMDB13 as a EcoRV-NcoI fragment.

The Zm13 promoter is also cloned as follows. Genomic DNA of Zea mays line H99 is prepared as described above. Using the genomic DNA as a substrate, the following two fragments are amplified by means of PCR: 1) a 875 bp fragment is amplified using the oligonucleotides MDB80 (SEQ ID No. 4) and ZM13OLI2 (which is complementary to nucleotides 859 to 882 of Zmg13 and which sequence is given in SEQ ID No. 11); and 2) a 661 bp fragment is amplified using the oligonucleotides Zm13OLI1 (which corresponds to nucleotides 767 to 791 of Zmg13 and which sequence is given in SEQ ID No. 12) and Zm13OLI5 (which is partially complementary to nucleotides 1397 to 1423 of Zmg13 and which sequence is given in SEQ ID No. 13). The 875 bp fragment, corresponding to the upstream region of the Zm13 promoter, is cloned into the SmaI site of pGEM2, yielding plasmid pTS204. The 661 bp fragment, corresponding to the downstream region of the Zm13 promoter, is digested with NcoI and cloned into plasmid pJB66 (Botterman and Zabeau (1987) DNA 6:583) digested with EcoRV and NcoI, yielding plasmid pTS203. Both fragments partly overlap and share a BstXI site in the region of overlap. Ligation of the 567 bp EcoRV-BstXI fragment of pTS204 and the 638 bp BstXI-NcoI fragment of pTS203 results in a 1205 bp fragment corresponding to the Zm13 promoter. This 1205 bp fragment, as cloned from line H99, is sequenced, and its sequence is found to be identical to the corresponding fragment of Zmg13 from line W-22 as given in SEQ ID No.1 except at position 276 (G in W-22 is T in H99), 410 (G in) W-22 is A in H99), and 1205–1206 (GC in W-22 is GGC in H99, thus corresponding to a 1 nucleotide insertion), numberings being as in SEQ ID No. 1.

Example 2
Construction of Plant Transformation Vectors Comprising a Maintainer Gene that Contain DNA Encoding Barstar Under the Control of the TA29 Promoter and DNA Encoding Barnase Under the Control of the Zm13 Promoter The 1205 bp EcoRV-NcoI fragment of pMDB13 is ligated to the large EcoRI-SmaI fragment of plasmid pVE144 and to the 739 bp EcoRI-NcoI fragment of pVE108, yielding plasmid pGSJVR1. Plasmid pVE144, the sequence of which is shown in SEQ ID no. 2, is a plasmid derived from plasmid pUC18 (Yanisch-Perron et al (1985) Gene 33:103) and containing DNA encoding neomycin phosphotranferase (neo) under the control of the 35S3 promoter (EP 0,359,617) from Cauliflower Mosaic Virus isolate CabbB-JI (Hull and Howell (1978) Virology 86:482) and DNA encoding the Barstar (Hartley (1988) J. Mol. Biol. 202:913) under the control of the tapetum-specific promoter of the TA29 gene of Nicotiana tabacum (EP 0,344,029; Seurinck et al (1990) Nucleic Acids Res. 18:3403). Plasmid pVE108, the sequence of which is shown in SEQ ID no. 3, is a plasmid derived from pUC18 and containing DNA encoding phosphinothricin acetyl transferase (bar) (EP 0,242,236) under the control of the 35S3 promoter and DNA encoding Barnase (Hartley (1980) supra) under the control of the TA29 promoter. The resulting plasmid, pGSJVR1 (which is subsequently renamed "pTS210"), is a pUC18-derived plasmid that contains a maintainer gene of this invention comprising: DNA encoding Barnase as the pollen-lethality DNA, the Zm13 promoter as the pollen-specific promoter, DNA encoding Barstar as the fertility-restorer DNA, the TA29 promoter as the restorer promoter, neo as the first marker DNA and the 35S3 promoter as the first marker promoter.

pTS210 is also obtained as follows. The 0.9 kb BstXI-SacI fragment of pTS204 is ligated to the large BstXI-SacI fragment of pTS203, yielding plasmid pTS206. The 1.47 BglII-NcoI kb fragment of pTS206 is then ligated to the large NcoI-BglII fragment of pVE108, yielding plasmid pTS207. Finally, the 1.9 kb EcoRV-Eco-RI fragment of pTS207 is ligated to the large Eco-RI-SmaI fragment of pVE144, yielding plasmid pTS210.

A plasmid pTS218, which differs from pTS210 by carrying the bar gene as a selectable marker gene, is also obtained as follows:

- a 255 bp DNA fragment, designated as bxx and carrying the translation initiation site of the PTA29-barstar gene, is obtained by PCR using pVE144 as a template and oligonucleotides BXOL2 (SEQ ID No. 14) and TA29SBXOL2 (SEQ ID No. 15) as primers.
- a 492 bp DNA fragment is prepared by PCR using pVE108 and bxx as a template and oligonucleotides PTA29OL5 (SEQ ID No. 16) and BXOL2 as primers. This 492 bp fragment is digested with AsnI and BspEI, and a 274 bp fragment is purified on gel and ligated to the 6.28 kb fragment of pVE144 which was digested with BspEI and partially digested with AsnI. The resulting plasmid is designated as pVEK144 and carries the PTA29-barstar-3'nos chimeric gene with an optimized translational initiation context.
- pVEK144 is digested with MunI and HindIII, and the 3.7 kbp fragment is isolated and ligated to the 1.7 kbp MunI-HindIII fragment of pVE180, yielding plasmid pVEB144 which carries the PTA29-barstar-3'nos and the P35S-bar-3'nos chimeric genes.
- the EcoRI-HindIII fragment of pVEB144, containing the two chimeric genes, is ligated to the large EcoRI-HindIII fragment of pUCNew2, yielding plasmid pVEC144. pUCNew2 is derived from pUC19 as described in WO 92/13956.
- finally, the large EcoRI-SmaI fragment of pVEC144 is ligated to the 1.9 bp EcoRV-EcoRI fragment of pTS207, yielding plasmid pTS218.

Plasmid pTS218 carries three chimeric genes, i.e., PTA29-barstar-3'nos (with optimized translational initiation context), P35S-bar-3'nos, and PZM13-barnase-3'nos. The EcoRI-HindIII fragment of pTS218 carrying these three chimeric genes is presented in the sequence listing as SEQ ID No. 17.

All steps of vector construction involving fragments of the barnase DNA, such as pVE108, pVE144, and pTS210, are carried out in E. coli strain MC1061 containing the cointegrate plasmid R702::pMc5BS which is obtained as follows. Plasmid pMc5BS, containing the barstar gene (encoding an inhibitor of barnase) under the control of the tac promoter (De Boer et al (1983) Proc. Natl. Acad. Sci. U.S.A. 80:21), is constructed by: cloning the EcoRI-HindIII fragment of plasmid pMT416 (Hartley (1988) supra) into the EcoRI and HindIII sites of plasmid pMc5–8 (DSM 4566); and then deleting the sequence starting with the initiation codon of the phoA signal sequence and ending with the last nucleotide before the translation initiation codon of the barstar-coding region by means of a looping-out mutagenesis procedure as generally described by Sollazo et al (1985) Gene 37:199.

Plasmid R702 is from *Proteus mirabilis* and can replicate in E. coli (Villarroel et al (1983) Mol. Gen. Genet. 189:390). Plasmid R702::pMc5BS is obtained by cointegration through illegitimate recombination between pMc5BS and R702, mediated by transposable elements present on R702 (Leemans (1982) "Technieken voor het gebruik van Ti-plasmieden van *Agrobacterium tumefaciens* als vectoren voor de genetic engineering van planten", Ph.D. Thesis Vrije Universiteit Brussel, Brussels, Belgium) and checked for induced expression of Barstar.

The use of E. coli, (R702::pMc5BS) allows the construction, maintenance, amplification, and purification of plasmids containing the barnase DNA, such as pGSJVR1, without any lethal effect on the host due to accidental expression of the barnase DNA. However, because the Zm13 promoter is not expressed in E. coli, all steps of vector construction involving this promoter are also carried out in E. coli strain MC1061.

Example 3

Transformation of Corn with the Maintainer Gene of Example 2

Zygotic immature embryos of about 0.5 to 1 mm are isolated from developing seeds of corn inbred line H99. The freshly isolated embryos are enzymatically treated for 1–2 minutes with an enzyme solution II (0.3% macerozyme (Kinki Yakult, Nishinomiya, Japan) in CPW salts (Powell & Chapman (1985) "Plant Cell Culture, A Practical Approach", R. A. Dixon ed., Chapter 3) with 10% mannitol and 5 mM 2-[N-Morpholino] ethane sulfonic acid (MES), pH 5.6). After 1–2 minutes incubation in this enzyme solution, the embryos are carefully washed with N6aph solution (macro- and micro-elements of N6 medium (Chu et al (1975) Sci. Sin. Peking 18:659) supplemented with 6 mM asparagine, 12 mM proline, 1 mg/l thiamine-HCl, 0.5 mg/l nicotinic acid, 100 mg/l casein hydrolysate, 100 mg/l inositol, 30 g/l sucrose and 54 g/l mannitol). After washing, the embryos are incubated in the maize electroporation buffer, EPM-KCl (80 mM KCl, 5 mM $CaCl_2$, 10 mM HEPES (N-2-hydroxyethylpiperazine-N'-2-ethanesulfonic acid) and 0.425 M mannitol, pH 7.2). Approximately 100 embryos in 200 $\mu$EPM-KCl are loaded in each electroporation cuvette. About 20 $\mu$g of a plasmid DNA, pPGSJVR1 (of Example 2) linearized with EcoRI, is added per cuvette.

After 1 hour DNA incubation with the explants, the cuvettes are transferred to an ice bath. After 10 minutes incubation on ice, the electroporation is carried out: one pulse with a field strength of 375 V/cm is discharged from a 900 $\mu$F capacitor. The electroporation apparatus is as described by Dekeyser et al (1990) The Plant Cell 2:591. Immediately after electroporation, fresh liquid N6aph substrate is added to the explants in the cuvette, after which the explants are incubated for a further 10 minute period on ice.

Afterwards, the embryos are transferred to Mah1 VII substrate (macro- and micro-elements and vitamins of N6 medium supplemented with 100 mg/l casein hydrolysate, 6 mM proline, 0.5 g/l MES, 1 mg/l 2,4-dichlorophenoxyacetic acid (2,4-D) and 2% sucrose solidified with 0.75 g/l $MgCl_2$ and 1.6 g/l Phytagel (Sigma Chemical Company, St Louis, Mo. U.S.A.), pH 5.8) and supplemented with 0.2M mannitol. After 3 days, the embryos are transferred to the same substrate supplemented with 200 mg/l kanamycin. After approximately 14 days, the embryos are transferred to Mah1 VII substrate without mannitol, supplemented with kanamycin. The embryos are further subcultured on this selective substrate for approximately 2 months with subculturing intervals of about 3 weeks. The induced embryogenic tissue is carefully isolated and transferred to MS medium (Murashige and Skoog (1962) Physiol. Plant 15:473) supplemented with 5 mg/l 6-benzylaminopurine for line H99. The embryogenic tissue is maintained on this medium for approximately 14 days and subsequently transferred to MS medium without hormones and 6% sucrose for line H99. Developing shoots are transferred to 1/2 MS medium with 1.5% sucrose for further development to normal plantlets. These plantlets are transferred to soil and cultivated in the greenhouse.

In an analogous way, corn embryos are transformed with a fragment of pTS218 DNA which contains the maintainer gene and the chimeric P35S-bar-3'nos and which is obtained by digestion of the plasmid with EcoRI, XhoI and PstI and by purifying the longest fragment. Transformation and plant regeneration is as described in Example 5.

Example 4
Analysis of the Transgenic Corn Plants of Example 3

Plants from Example 3 transformed with pGSJVR1 are analysed for the presence of the maintainer gene by means of PCR. DNA is prepared according to the protocol described by Dellaporta et al (1983) Plant Mol. Biol. Reporter 1:19, adapted for application to tissue amounts of about 10 to 20 mg. For each plant, such an amount of tissue is macerated in extraction buffer in a microfuge tube. Representative fragments of the maintainer gene are amplified using appropriate oligonucleotide probes.

Activity of the expression product of the first marker gene (i.e., neomycin phosphotransferase II (NPTII)) is assayed in plants as follows. Crude extracts are prepared by grinding plant tissue in extraction buffer (McDonnell et al (1987) Plant Molecular Biol. Reporter 5:380). The extracts are then subjected to non-denaturing polyacrylamide gel electrophoresis according to the procedure described by Reiss et al (1984) Gene 30:211. NPTII activity is then assayed by in situ phosphorylation of kanamycin using [gamma-32P]ATP as a substrate (McDonnell et al (1987) supra).

The plants that are found to be positive in both the PCR and NPTII assays are further analyzed by means of Southern hybridization. Genomic DNA is prepared from plant tissue according to the protocol described by Dellaporta et al (1983) supra, supplemented by a treatment with RNase to remove remaining RNA. A non-transformed H99 plant is used as a control. Samples of the DNA are digested with appropriate restriction enzymes and subjected to horizontal agarose electrophoresis. Southern transfer to Hybond N+ (Amersham International PLC, Amersham, United Kingdom) membranes by means of the "alkali blotting of DNA" protocol and the subsequent hybridization are performed as recommended by the manufacturer (Amersham Hybond-N+ leaflet). Suitable radioactive probes are prepared with the multi-prime DNA labelling kit (Amersham) according to the protocol supplied by the manufacturer which is derived from published procedures (Feinberg and Vogelstein (1983) Anal. Biochem. 132:6). The banding patterns show that at least the maintainer gene is integrated into the plant genomic DNA.

The PCR assays show that the maintainer gene is present. The NPTII assays show that the first marker DNA is expressed. The mature transformed plants can then be analyzed phenotypically to see whether the barstar DNA is expressed in tapetum cells and the barnase gene is expressed in pollen cells. Expression of barstar is determined by northern blotting of anther mRNA and by making testcrosses to determine the restoration in the progeny. Expression of the pollen-lethality gene is determined by cytological examination of the anther. In this regard, viable and nonviable mature pollen is determined by analyzing the staining of isolated pollen upon incubation for 30 minutes at 24° C. in the following reaction mixture: 100 mm phosphate buffer pH 7.8, 100 mm Sodiumsuccinate and 1 mM NitroBlue Tetrazolium, followed by visual inspection of formazan precipitation in viable pollen. Alternative techniques for the differentiation between viable and nonviable mature pollen are those described, for example, by Alexander (1969) Stain Technology 44:117, and by Heslop-Harrison and Heslop-Harrison (1970) Stain Technology 45:115. The viability of microspores is determined by embedding flower buds in plastic at different developmental stages and subjecting the buds to histochemical staining with the succinate dehydrogenase assay, both as described by De Block and Debrouwer (1992) The Plant Journal 2:261.

Ultimately, the progeny of the plant transformed with the pollen-lethality gene is determined. None of the offspring obtained from a cross using this plant as a male parent have this gene, while 50% of the offspring obtained from a cross using this plant as a female parent possess the gene.

Plants from Example 3, transformed with pTS218 DNA, are analyzed in the same way, except that the expression product of the first marker gene, i.e., phosphinothricine acetyltransferase, is assayed by means of a PAT assay as described in Example 5.

Example 5
Production of Male-sterile Corn Plants

Zygotic embryos of corn inbred line H99 were isolated, enzymatically treated, washed, and loaded in electroporation buffer as described in Example 3. Approximately 100 embryos in 200 $\mu$l EPM-KCl were loaded in each electroporation cuvette. About 20 $\mu$g of a plasmid DNA, pVE108 linearized with HindIII, was added per cuvette. pVE108 is a 5620 bp plasmid which contains: a chimaeric gene comprising the bar DNA (EP 242236), encoding phosphinothricin acetyl transferase (PAT) and conferring resistance to an herbicidal glutamine synthetase inhibitor such as phosphinothricin (PPT), under the control of the 35S3 promoter; and another chimaeric gene comprising the DNA coding for barnase (Hartley (1988) supra) under the control of the tapetum-specific promoter of the TA29 gene (EP 344029) of N. tabacum. The complete sequence of plasmid pVE108 is given in SEQ ID no. 4. All vector constructions involving DNA fragments comprising the barnase gene were carried out in E. coli strain MC1061 containing the plasmid R702::pMc5BS of Example 3. After a 1 hour DNA incubation with the explants, the cuvettes were transferred to an ice bath. After 10 minutes incubation on ice, the electroporation was carried out as described in Example 3. Immediately after electroporation, fresh liquid N6aph substrate was added to the explants in the cuvette, after which the explants were incubated for a further 10 minute period on ice.

Afterwards, the embryos from one electroporation experiment were transferred to Mah1 VII substrate supplemented with 0.2 M mannitol and 2 mg/l PPT. After approximately 14 days, the embryos were transferred to Mh1 VII substrate (Mah1 VII substrate of Example 3 but without proline and casein hydrolysate) supplemented with 2 mg/l PPT but without mannitol. After approximately 4 weeks, the embryos were subcultured for another month on Mh1 VII substrate supplemented with 10 mg/l PPT. The induced embryogenic tissue was carefully isolated and transferred to MS medium supplemented with 5 mg/l 6-benzylaminopurine. The embryogenic tissue was maintained on this medium for approximately 14 days and subsequently transferred to MS medium without hormones and sucrose. Developing shoots were transferred to 1/2 MS medium with 1.5% sucrose for further development to normal plantlets. These plantlets survived an in vitro spraying with doses of BASTA$^R$ (Hoechst AG, Frankfurt am Main, Germany) corresponding to 2 l/ha. These plantlets were then transferred to soil and cultivated in the greenhouse, and two of the transformed plantlets, designated RZM35-1 and RZM35-18, were further characterized.

The embryos from a second electroporation experiment were transferred to Mh1 VII substrate supplemented with 2 mg/l PPT and 0.2 M mannitol. After about 14 days, the embryos were transferred to Mh1 VII substrate supplemented with 2 mg/l PPT but without mannitol. After approximately another three weeks, the embryos were transferred to Mh1 VII substrate supplemented with 10 mg/l PPT but without mannitol. After another three weeks, the induced embryogenic tissue was carefully isolated and transferred to MS medium supplemented with 2 mg/l PPT and 5 mg/l 6-benzylaminopurine. The embryogenic tissue was maintained on this medium for approximately 14 days and subsequently transferred to MS medium without hormones, sucrose or PPT. Developing shoots were transferred to 1/2 MS medium with 1.5% sucrose for further development to normal plantlets. The resulting plantlets were transferred to soil and cultivated in the greenhouse, and three of the transformed plantlets, designated RZM34-1, RZM34-12, and RZM34-14, were further characterized.

RZM34-1, RZM34-12, RZM34-14, RZM35-1, and RZM35-18 were grown in the greenhouse. Activity of the expression product of the bar gene in leaves of the plants was assayed as follows in a "PAT assay". 100 mg of leaf tissue from each plant, together with 50 mg of acid-treated sea sand (Merck, Darmstadt, Germany) and 5 mg polyvinylpolypyrrolidone (PVPP), were ground in an Eppendorf tube with a glass rod in 50 $\mu$l of extraction buffer (25 mM Tris-HCL pH 7.5, 1 mM $Na_2$-EDTA (ethylenediaminetetraacetic acid disodium salt), 0.15 mg/ml phenylmethylsulfonylfluoride (PMSF), 0.3 mg/ml dithiothreitol (DTT), and 0.3 mg/ml bovine serum albumin). The extract was centrifuged in a microfuge for 5 minutes at 16,000 rpm. The supernatant was recovered and diluted ten times with TE 25/1 (25 mM Tris-HCL pH 7.5, 1 mM $Na_2$-EDTA. To twelve $\mu$l of the diluted extract was then added: 1 $\mu$l of 1 mM PPT in TE 25/1, 1 $\mu$l of 2 mM AcetylCoenzyme A in TE 25/1, and 2 $\mu$l of [14C] AcetylCoenzym A (60 mCi/mmol, 0.02 mCi/ml, [NEN Research Products, Dupont, Wilmington, Del., U.S.A.). The reaction mixture was incubated for 30 minutes at 37° C. and spotted on a aluminium sheet silica gel 60 t.l.c. plate with concentrating zone (Merck). Ascending chromatography was carried out in a 3 to 2 mixture of 1-propanol and $NH_4OH$ (25% $NH_3$). $14_C$ was visualized by overnight autoradiography (XAR-5 Kodak film). The tolerance to the herbicide BASTA$^R$ was tested by rushing a small area near the top of one leaf per plant with a 1% solution of the herbicide and observing the damage symptoms at and near the brushed sites. While RZM34-1, RZM35-1 and RZM35-18 showed no damage symptoms at all, RZM34-12 and RZM34-14 displayed slight browning and drying-out of the brushed site. RZM34-1, RZM34-12, RZM34-14, RZM35-1 and RZM35-18 were also shown to be male-sterile but otherwise phenotypically completely normal; female fertility, for instance, was normal. The spikelets of the male flowers were of about normal length but were very thin and appeared to be empty, and they never opened. A detailed analysis showed that the anthers were reduced to almost microscopic structures. This phenotype indicates not only that at least one copy of the barnase gene was expressed, but also that it was selectively expressed in some or all of the tissues of the anthers.

Southern analysis showed RZM35-1 and RZM35-18 to have an identical integration pattern, with only one copy of plasmid pVE108 being present in the genome of each plant. A small part of the plasmid DNA sequence adjacent to the HindIII site (used for linearization prior to electroporation) seemed to be absent in the integrated copy. Southern analysis of RZM34-1, RZM34-12 and RZM34-14 showed that each of these plants probably has two or three copies of part or all of pVE108 integrated into its genome. The copies are most likely not inserted in a concatemer configuration.

Transformants RZM35-1 and RZM34-1 were pollinated with pollen from an untransformed H99 plant, and progeny plantlets were recovered. From the 35 plantlets recovered from RZM35-1, 16 (46%) scored positive in a PAT assay, while 19 (54%) were PAT negative. This proportion in the F1 progeny does not differ significantly from the 1:1 ratio expected under normal Mendelian segregation of one active copy of the chimaeric bar gene (X2=0.26).

From the 34 plantlets recovered from RZM34-1, 19 (56%) scored positive in a PAT assay, while 15 (44%) were PAT negative. This proportion in the F1 progeny does not differ significantly from the 1:1 ratio expected under normal Mendelian segregation, assuming that the transformed female parent had one active copy, or alternatively multiple active, but closely linked copies, of the chimaeric bar gene (X2=0.47).

Example 6

Production of Restorer Corn plants

Zygotic embryos of corn inbred line H99 were isolated, enzymatically treated, washed and loaded in electroporation buffer as described in Example 5. Approximately 100 embryos in 200 $\mu$l EPM-KCl were loaded in each electroporation cuvette. About 20 $\mu$g of a plasmid DNA, pVE144 linearized with HindIII, was added per cuvette. pVE144 is a 6555 bp plasmid which was described in Example 2.

The embryos were electroporated, and the transformed cells were selected, grown into callus, and regenerated as described in Example 3. Transgenic plants were analyzed for the presence of the fertility-restorer gene and the marker gene by means of Southern hybridization and PCR. The expression of the fertility-restorer gene is assayed by means of Northern blotting, and the expression of the marker gene is determined by NPTII assay as described in Example 3.

Example 7

Production of Maintainer Corn Plants and a Male-sterile Corn Line and Maintenance of the Male-sterile Corn Line Maintainer plants of this invention of corn line H99 are obtained as outlined in FIG. 1. A plant of corn inbred line H99 with the male-sterility genotype $H99^{S/s,r/r,p/p}$, transformed with the male-sterility gene of Example 5, is crossed with plants with the genotype $H99^{s/s,R/r,p/p}$, transformed with the fertility-restorer gene of Example 6. The progeny that have the genotype $E99^{S/s,R/r,p/p}$ are identified by PCR analysis for the presence of the S and R genes. These plants are selfed, yielding progeny with nine different genotypes. Two of these genotypes ($H99^{S/S,r/r}$ and $H99^{S/s,r/r}$) will develop into male-sterile plants, while all the other genotypes will develop into male-fertile plants. When these male-fertile plants are selfed, progeny analysis allows the identification of their genotype. Thus: a) the progeny of selfings of $H99^{S/S,R/R}$, $H99^{S/s,R/R}$, $H99^{s/s,R/R}$, $H99^{s/s,R/r}$ and $H99^{s/s,r/r}$ would all develop into male-fertile plants; b) selfings of $H99^{S/s,R/r}$ plants would produce progeny, of which 13 out of 16 would be male-fertile, and since the male-sterility gene is linked to the herbicide resistance gene, bar, 4 out of the 13 male-fertile plants would be sensitive to the herbicide BASTA$^R$; and c) selfings of $H99^{S/S,R/r}$ plants would produce progeny, of which 12 out 16 would be fertile (4 out of 16 would have the genotype H99$^{S/S,R/R}$ and 8 out of 16 would have the genotype H99$^{S/S,R/r}$), all of which would be resistant to the herbicide, and the male-sterile progeny of which (4 out of 16) would all be homozygous for the male-sterility gene (H99S/S,r/r).

The homozygous male-sterile progeny (H99$^{S/S,r/r}$) of selfing (c) are then crossed with their male-fertile siblings, and only when the cross is with plants with the genotype H99$^{S/S,R/r}$ are the resulting plants 50% male-sterile (all with the genotype H99$^{S/S,r/r}$) and 50% male-fertile (all with the genotype H99$^{S/S,R/r}$. Indeed, the alternative cross between H99$^{S/S,r/r}$ and H99$^{S/S,R/R}$ would result in 100% male-fertile progeny plants.

Maintainer plants are selected by crossing the plant with the genotype H99$^{S/s,R/r,p/p}$ with a plant that is heterozygous for the maintainer gene of Example 2, i.e., (H99$^{s/s,r/r,P/p}$), using the latter plant as the female parent. The offspring with the genotype H99$^{S/s,r/r,P/p}$ are selected by means of testcrosses supplemented with PCR analysis of the progeny (which can be easily identified by PCR and Southern blotting for the presence of the S and P genes and the absence of the R gene). The selected fertile offspring are then selfed. One out of eight offspring have the desired genotype for a maintainer plant of this invention (H99$^{S/S,P/p}$) and can be further selected by means of testcrosses and PCR analysis of the progeny. Indeed, only plants with this genotype will produce 50% male-sterile offspring (all H99$^{S/S,p/p}$) and 50% male-fertile offspring (all H99$^{S/S,P/p}$), thus growing at once both the desired homozygous male-sterile line and the maintainer line of this invention. Testcrosses also include the pollination of wild type H99 plants with pollen of the progeny plants obtained from the selfing of H99$^{S/s,P/p}$ plants.

Homozygous male-sterile plants with the genotype H99$^{S/S,r/r,p/p}$ are then pollinated by maintainer plants H99$^{S/S,r/r,P/p}$) of this invention. All progeny have the genotype H99$^{S/S,r/r,p/p}$, so that the male-sterile line is maintained, as desired.

Example 8
Introduction of the Male-sterility Gene and the Maintainer Gene in Inbred Corn Lines Through Classical Breeding The male-sterility gene of Example 5 and the maintainer gene of Example 2 are transferred from corn inbred line H99 to another corn inbred line (A) by repeated backcrossings as follows. The maintainer plant H99$^{S/S,P/p}$ is crossed as a female parent with an untransformed plant of line A (A$^{s/s,p/p}$). The offspring with the genotype A-H99$^{S/s,P/p}$ are selected by screening, using PCR, for the presence of both the maintainer gene (P) and the male-sterility gene (S). These plants are then crossed again as female parents with A$^{s/s,p/p}$ plants, and the offspring that are heterozygous for both the P and S genes are again selected by PCR. This process of backcrossing is repeated until finally plants with the genotype A$^{S/s,P/p}$ are obtained. These plants are then selfed, and the progeny are analyzed in the same way as described in Example 7. In this way, male-sterile plants with the genotype A$^{S/S,p/p}$ and maintainer plants of this invention with the genotype A$^{S/S,P/p}$ are obtained.

TABLE 1

| | | |
|---|---|---|
| 1. | Action | Transform corn embryos (e.g. H99) with male-sterility gene S. linked to herbicide resistance gene bar (Example 5) |
| | Result | transformed plants with genotype S/s |
| 2. | Action | Transform corn embryos (e.g. H99) with fertility-restorer gene R (Example 6) |

TABLE 1-continued

| | | |
|---|---|---|
| | Result | transformed plants with genotype R/r |
| 3. | Action | Transform corn embryos (e.g; H99) with maintainer gene P (Example 3) |
| | Result | transformed plants with genotype P/p |
| 4. | Action | Cross S/s, r/r × s/s R/r. Select offspring for presence of both S and R genes by means of PCR. |
| | Result | plants with genotype S/s, R/r |
| 5. | Action | Self selected plants of 4 (optional) |
| | Result | Progeny plants with 9 different genotypes |

| gamete ♀ ♂→ ↓ | S,R | S,r | s,R | s,r |
|---|---|---|---|---|
| S, R | S/S, R/R | S/S, R/r | S/s, R/R | S/s, R/r |
| S, r | S/S, R/r | S/S, r/r** | S/s, R/r | S/s, r/r** |
| s, R | S/s, R/R | S/s, R/r | s/s, R/P | s/s, R/r |
| s, r | S/s, R/r | S/s, r/r** | s/s, R/r | s/s, r/r |

**male-sterile plants

| | | |
|---|---|---|
| 6. | Action | self male-fertile progeny plants of 5 (Optional) |
| | Result | |
| 6.1. | Self of S/S, R/R: | 100% male-fertile plants |
| | Self of S/s, R/R: | 100% male-fertile plants |
| | Self of s/s, R/R: | 100% male-fertile plants |
| | Self of s/s, R/r: | 100% male-fertile plants |
| | Self of s/s, r/r: | 100% male-fertile plants |
| 6.2 | Self of S/s, R/r: | Same progeny as in 5 13/16 male-fertile plants with 4/13 herbicide sensitive |
| 6.3 | Self of S/S, R/r: | Progeny as follows: |

| gamete ♀ ♂→ ↓ | S,R | S,r |
|---|---|---|
| S, R | S/S, R/R | S/S, R/r |
| S, r | S/S, R/r | S/S, r/r** |

**male-sterile plants
Thus: 3/4 male-fertile plants, 0% herbicide sensitive
All male-sterile plants are of genotype S/S, r/r

| | | |
|---|---|---|
| 7. | Action | Cross ♀: P/p (from 3) × ♂: S/s, R/r (from 4) this equals in fact ♀: s/s, r/r, P/p × ♂: S/s, R/r, p/p |
| | Result | Progeny with the following genotypes |

| gamete ♀ ♂→ ↓ | S,R,p | S,r,p | s,R,p | s,r,p |
|---|---|---|---|---|
| s, r, P | S/s, R/r, P/p | S/s, r/r, P/p | s/s, R/r, P/p | s/s, r/r, P/p |
| s, r, p | S/s, R/r, p/p | S/s, r/r, p/p | s/s, R/r, p/p | s/s, r/r, p/p |

| | | |
|---|---|---|
| 8. | Action | From offspring of 7, select plants with genotype S/s, r/r, P/p by screening, by means of PCR and/or Southern blotting, for presence of S and P gene and absence of R gene. |
| | Result | plants with genotype S/s, P/p |
| 9. | Action | Self plants with genotype S/s, P/p (from 8) |
| | Result | progeny with the following genotypes |

| gamete ♀ ♂→ ↓ | S,P | S,p | s,P | s,p |
|---|---|---|---|---|
| S, P | ▓▓▓▓ | S/S, P/p | ▓▓▓▓ | S/s, P/p |
| S, p | ▓▓▓▓ | S/S, p/p** | ▓▓▓▓ | S/s, p/p** |
| s, P | ▓▓▓▓ | S/s, P/p | ▓▓▓▓ | s/s, P/p |

TABLE 1-continued

| | | | | |
|---|---|---|---|---|
| s, p | ░S/s,P/p░ | S/s, p/p** | ░S/s,P/p░ | s/s, p/p |

**male-sterile plants

Shaded genotypes cannot develop because male gametes (pollen) are killed off by expression of the maintainer gene P.

10. Action    self male fertile plants of 9.
    Result
    10.1.    Self of s/s, P/p:    100% male-fertile plants
             Self of s/s, p/p:    100% male-fertile plants
    10.2     Self of S/s, P/p:    Same progeny as in 9 5/8 male-fertile plants with 2/5 herbicide sensitive
    10.3     Self of S/S, P/p:    Progeny as follows

| gamete | S,P | S,p |
|---|---|---|
| ♂ ♀→ | | |
| ↓ | | |

TABLE 1-continued

| | | |
|---|---|---|
| S, P | ░S/S,P/P░ | S/S, P/p |
| S, p | ░S/S,P/p░ | S/S, p/p** |

**male-fertile plants

Shaded genotypes cannot develop because male gametes (pollen) are killed off by expression of the maintainer gene P.

FINAL RESULT

1/2 male-fertile plants, 0% herbicide sensitive. All these plants are maintainer plants 1/2 male sterile plants. All homozygous for the male-sterility gene S.

---

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 2661 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iii) ANTI-SENSE: NO (vi) ORIGINAL SOURCE:
      (A) ORGANISM: Zea mays
      (B) STRAIN: inbred line W-22

(x) PUBLICATION INFORMATION:
      (A) AUTHORS: Hamilton et al.,
      (C) JOURNAL: Sex Plant Reprod.
      (D) VOLUME: 2
      (F) PAGES: 208-
      (G) DATE: 1989

(xi) SEQUENCE DESCRIPTION: SEQ ID NO: 1:

```
AAAGACCCCG CTTGTCAGTG AATGTTGCTA TTCTAGCAAA GGGAAGGTAT TTTTTCGGAC      60

CTTCGGCGTA AAGCCTTCGT CCAGATCGCA ATCTAAATTT ATTATTTTGA ACAAATTAAT     120

ATTGCGAGGG GCTACTGTTG GGGACCTTCG GCATCCGAAG GTCCTCAAAA ACAGGATTTA     180

ATAGTGTTTC TGGAGTATAA TGTGTGAACA GATATCTTCG GACTCAAGTC AGGCATCACA     240

GTAGACCAGA ATAATACGAA GGTTGGTGAA GCGCCGAAGG TGTAAGCAGG AAAGCTTCGG     300

CAAGACAGCA GCAGTTGAAA CCGACTTAAA GATGAAAAGG CTATTTAGAC CTCAACAGAT     360

TACTATAGGT TTATTATTAA GTGTAAAGGG CATTAATGTA ATTTTGCACG GGCTACGTCC     420
```

```
CGTGCCTATA AATAGGTGAA CAGTATTCCC GTACTGTTCA CGCTGACTTG GCATTCGCTT        480

TTTGCGTCAC GCTTGTACTG TCATCTCATT CCTATTGAAG GTACACTTGT AATTCAACGA        540

TATTTCTGTT TGTACCTAAT AATAATATAT AATTGTTCAT GTTGTCTTTT ATATTCTTTA        600

TATTTCATCC TTCGTCATTG TTTAATGAAT TTATGAAGGT ACGTCCTTCA TAACCTTCGT        660

CCGTAAACCA TTATATCCTA AGGGAAATAA TGCTTCGAAG GACGAAGGAC CTTAACGATT        720

AATATTTTCT ATGTTGCCTT GTTCTTAACT CATAGCACTT GAGAACAAGT CTCCAACAGT        780

TTGGTTATTC CTATTCCACG TGGATTAGAT GAGATTTAGA TAAAATTAGA AATAATTTTG        840

ACTTACTAGG GATTTAAACC AACTCAGTCC CGTTCAATCC ACATGGATTG AGATTAAAAC        900

AACTATTGAG ATTTTATTGT ATCAACACTC AACACCGATG TGTTTTTATA ATACATCTTG        960

CGTGACATTT GTCCAAGTAC TATGCTAAAT ATGAGAAGCT GCCATTTAGT GATTCTATAT       1020

ACTATTCACT TATGGATACA TTTAACTGAT ACCGTTTTGT TGAGCGCGTC TTATTTAGTT       1080

TTACATAGCA GCATAGAAGA TTAGAAGTCG CAAATCCAAC TTTTGTGGAC CGCTGAAAAA       1140

CTCAACCAAA TTCGACATAT TTTTCACCTC CCCATGCCAC AAAACTAGGT CAAAACGGCT       1200

TTCTGCCGTC GGCCACTATT TCTACGGGCA GCCAGACAAA TCTTCGGGTC TCGCAGATTA       1260

TTTAAGGACA CCACAGGCTG CGTTACGAAA CCAGGCCAGA TTTGCCACCC TCGTCTCACC       1320

CTCCCTCCCT CACACAAATA ATAAGGAAAG GTCCCGCCCT TTTCCTCCGA CATCCACAAG       1380

GGGGGAGGGG AAAACACGTA CATTCACCCG GCGGCAATAA TGGCCTCGGT TCCGGCTCCG       1440

GCGACGACGA CCGCCGCCGT CATCCTATGC CTATGCGTCG TCCTCTCCTG TGCCGCGGCT       1500

GACGACCCGA ACCTCCCCGA CTACGTCATC CAGGGCCGCG TGTACTGCGA CACCTGCCGC       1560

GCCGGGTTCG TGACCAACGT CACCGAGTAC ATCGCGGGCG CCAAGGTGAG GCTGGAGTGC       1620

AAGCACTTCG GCACCGGCAA GCTCGAGCGC GCCATCGACG GGGTCACCGA CGCGACCGGC       1680

ACCTACACGA TCGAGCTCAA GGACAGCCAC GAGGAGGACA TCTGCCAGGT GGTGCTGGTG       1740

GCCAGCCCGC GCAAGGACTG CGACGAGGTC CAGGCGCTCA GGGACCGCGC CGGCGTCCTG       1800

CTCACCAGGA ACGTTGGCAT CTCCGACAGC CTGCGCCCCG CCAACCCGCT AGGCTACTTC       1860

AAGGACGTGC CGCTCCCCGT CTGCGCCGCG CTGCTCAAGC AGCTGGACTC GGACGACGAC       1920

GACGACCAGT AAACTATACC ACGGCGGCGT CGCGGACATG CTGCACAAAA CTACAACGAT       1980

ACAGAGCGAA CGCATGGCAT GGATAGCAGT ATCTACGGAA AGAAAAGGAA GAAAAGGAAA       2040

ATAAAAAATG TATCAGAGTG CTTGATTCAC TTGCTGCTGT CACCCATTCC CCGTTCTTAA       2100

CATAACATGT GGGCCGGCTT GGCCCAGGCA CAAGCCCATC TACGCATGGC CTACGGTCCG       2160

CTAAAATATA GCCCTAATTA TGAGCCGTGT TGTGCCGTCA CATGGATCGA TCCAGCGGCA       2220

TACGATACAA CCCACAATTA CTTATGTGTG ATGGGCCGGC CAAAAAAGCC TAAGATGTCG       2280

TAGTGTGCTA GACCGACTCA TATATATAAA ACATTAAAAC ATATTGTCGG GGACCATAAT       2340

TAGGGGTACC CTTAAGGCTC CTAATTCTCA GCTGGTAACC CTCATCAGCG TAAAGCTGCA       2400

AAGGCCTGAT GGGTGCGATT AAGTCAGGGA TCAGTCCATT CGAGGGACTC GATCACGCCT       2460

CGCCCGAGCC TAGCCTCGGA CAAGGGCAGC CGACCCCGGA GGATCTCCGT CTCGCCCGAG       2520

GCCCTCCTCC AGCGGCGAAC ATATTTCCGG CTCGCCCGAG GCCCTGTCTT CGCCAAGAAG       2580

CAACCCTGAC CAAATCGCCG CACCGACCGA CCAAATCGCG GGAGCATTTA ATGCAAAGGT       2640

GGCCTGACAC ATTTATCCTG A                                                 2661
```

(2) INFORMATION FOR SEQ ID NO: 2:

(i) SEQUENCE CHARACTERISTICS:

(A) LENGTH: 6555 base pairs
          (B) TYPE: nucleic acid
          (C) STRANDEDNESS: double
          (D) TOPOLOGY: circular (ii) MOLECULE TYPE: DNA (genomic)

(iii) HYPOTHETICAL: NO (iii) ANTI-SENSE: NO (vi) ORIGINAL SOURCE:
          (A) ORGANISM: plasmid pVE144 (replicable in E.coli)

(ix) FEATURE:
          (A) NAME/KEY: -
          (B) LOCATION: 1..396
          (D) OTHER INFORMATION: /label= pUC18
              /note= "pUC18 derived sequence"

(ix) FEATURE:
          (A) NAME/KEY: -
          (B) LOCATION: complement (397..751)
          (D) OTHER INFORMATION: /label= 3'nos
              /note= "3' regulatory sequence containing the
              polyadenylation site derived from Agrobacterium
              T-DNA nopaline synthase gene"

(ix) FEATURE:
          (A) NAME/KEY: -
          (B) LOCATION: complement (752..1024)
          (D) OTHER INFORMATION: /label= barstar
              /note= "coding region of the barstar gene of
              Bacillus amyloliquefaciens"

(ix) FEATURE:
          (A) NAME/KEY: -
          (B) LOCATION: complement (1025..1607)
          (D) OTHER INFORMATION: /label= TA29
              /note= "promoter derived from the TA29 gene of
              Nicotiana tabacum"

(ix) FEATURE:
          (A) NAME/KEY: -
          (B) LOCATION: 1608..2440
          (D) OTHER INFORMATION: /label= 35S3
              /note= "35S3 promoter sequence derived from
              cauliflower mosaic virus isolate CabbB-JI"

(ix) FEATURE:
          (A) NAME/KEY: -
          (B) LOCATION: 2441..3256
          (D) OTHER INFORMATION: /label= neo
              /note= "coding region of the neomycine
              phosphotransferase gene of Tn5"

(ix) FEATURE:
          (A) NAME/KEY: -
          (B) LOCATION: 3257..4315
          (D) OTHER INFORMATION: /label= 3'ocs
              /note= "3' regulatory sequence containing the
              polyadenylation site derived from Agrobacterium
              T-DNA octopine synthase gene"

(ix) FEATURE:
          (A) NAME/KEY: -
          (B) LOCATION: 4316..6555
          (D) OTHER INFORMATION: /label= pUC18
              /note= "pUC18 derived sequence"

(xi) SEQUENCE DESCRIPTION: SEQ ID NO: 2:

TCGCGCGTTT CGGTGATGAC GGTGAAAACC TCTGACACAT GCAGCTCCCG GAGACGGTCA      60

CAGCTTGTCT GTAAGCGGAT GCCGGGAGCA GACAAGCCCG TCAGGGCGCG TCAGCGGGTG     120

TTGGCGGGTG TCGGGCTGG CTTAACTATG CGGCATCAGA GCAGATTGTA CTGAGAGTGC     180

ACCATATGCG GTGTGAAATA CCGCACAGAT GCGTAAGGAG AAAATACCGC ATCAGGCGCC     240

```
ATTCGCCATT CAGGCTGCGC AACTGTTGGG AAGGGCGATC GGTGCGGGCC TCTTCGCTAT    300

TACGCCAGCT GGCGAAAGGG GGATGTGCTG CAAGGCGATT AAGTTGGGTA ACGCCAGGGT    360

TTTCCCAGTC ACGACGTTGT AAAACGACGG CCAGTGAATT CGAGCTCGGT ACCCGGGGAT    420

CTTCCCGATC TAGTAACATA GATGACACCG CGCGCGATAA TTTATCCTAG TTTGCGCGCT    480

ATATTTGTT TTCTATCGCG TATTAAATGT ATAATTGCGG GACTCTAATC ATAAAAACCC    540

ATCTCATAAA TAACGTCATG CATTACATGT TAATTATTAC ATGCTTAACG TAATTCAACA    600

GAAATTATAT GATAATCATC GCAAGACCGG CAACAGGATT CAATCTTAAG AAACTTTATT    660

GCCAAATGTT TGAACGATCT GCTTCGGATC CTCTAGACCA AGCTAGCTTG CGGGTTTGTG    720

TTTCCATATT GTTCATCTCC CATTGATCGT ATTAAGAAAG TATGATGGTG ATGTCGCAGC    780

CTTCCGCTTT CGCTTCACGG AAAACCTGAA GCACACTCTC GGCGCCATTT TCAGTCAGCT    840

GCTTGCTTTG TTCAAACTGC CTCCATTCCA AAACGAGCGG GTACTCCACC CATCCGGTCA    900

GACAATCCCA TAAAGCGTCC AGGTTTTCAC CGTAGTATTC CGGAAGGGCA AGCTCCTTTT    960

TCAATGTCTG GTGGAGGTCG CTGATACTTC TGATTTGTTC CCCGTTAATG ACTGCTTTTT   1020

TCATCGGTAG CTAATTTCTT TAAGTAAAAA CTTTGATTTG AGTGATGATG TTGTACTGTT   1080

ACACTTGCAC CACAAGGGCA TATATAGAGC ACAAGACATA CACAACAACT TGCAAAACTA   1140

ACTTTTGTTG GAGCATTTCG AGGAAAATGG GGAGTAGCAG GCTAATCTGA GGGTAACATT   1200

AAGGTTTCAT GTATTAATTT GTTGCAAACA TGGACTTAGT GTGAGGAAAA AGTACCAAAA   1260

TTTTGTCTCA CCCTGATTTC AGTTATGAA ATTACATTAT GAAGCTGTGC TAGAGAAGAT   1320

GTTTATTCTA GTCCAGCCAC CCACCTTATG CAAGTCTGCT TTTAGCTTGA TTCAAAAACT   1380

GATTTAATTT ACATTGCTAA ATGTGCATAC TTCGAGCCTA TGTCGCTTTA ATTCGAGTAG   1440

GATGTATATA TTAGTACATA AAAAATCATG TTTGAATCAT CTTTCATAAA GTGACAAGTC   1500

AATTGTCCCT TCTTGTTTGG CACTATATTC AATCTGTTAA TGCAAATTAT CCAGTTATAC   1560

TTAGCTAGAT GGGGATCCTC TAGAGTCGAC CTGCAGGCAT GCAAGCTCCT ACGCAGCAGG   1620

TCTCATCAAG ACGATCTACC CGAGTAACAA TCTCCAGGAG ATCAAATACC TTCCCAAGAA   1680

GGTTAAAGAT GCAGTCAAAA GATTCAGGAC TAATTGCATC AAGAACACAG AGAAAGACAT   1740

ATTTCTCAAG ATCAGAAGTA CTATTCCAGT ATGGACGATT CAAGGCTTGC TTCATAAACC   1800

AAGGCAAGTA ATAGAGATTG GAGTCTCTAA AAAGGTAGTT CCTACTGAAT CTAAGGCCAT   1860

GCATGGAGTC TAAGATTCAA ATCGAGGATC TAACAGAACT CGCCGTGAAG ACTGGCGAAC   1920

AGTTCATACA GAGTCTTTTA CGACTCAATG ACAAGAAGAA AATCTTCGTC AACATGGTGG   1980

AGCACGACAC TCTGGTCTAC TCCAAAAATG TCAAAGATAC AGTCTCAGAA GACCAAAGGG   2040

CTATTGAGAC TTTTCAACAA AGGATAATTT CGGGAAACCT CCTCGGATTC CATTGCCCAG   2100

CTATCTGTCA CTTCATCGAA AGGACAGTAG AAAAGGAAGG TGGCTCCTAC AAATGCCATC   2160

ATTGCGATAA AGGAAAGGCT ATCATTCAAG ATGCCTCTGC CGACAGTGGT CCCAAAGATG   2220

GACCCCCACC CACGAGGAGC ATCGTGGAAA AGAAGACGT TCCAACCACG TCTTCAAAGC   2280

AAGTGGATTG ATGTGACATC TCCACTGACG TAAGGGATGA CGCACAATCC CACTATCCTT   2340

CGCAAGACCC TTCCTCTATA TAAGGAAGTT CATTTCATTT GGAGAGGACA CGCTGAAATC   2400

ACCAGTCTCT CTCTATAAAT CTATCTCTCT CTCTATAACC ATGGATCCGG CCAAGCTAGC   2460

TTGGATTGAA CAAGATGGAT TGCACGCAGG TTCTCCGGCC GCTTGGGTGG AGAGGCTATT   2520

CGGCTATGAC TGGGCACAAC AGACAATCGG CTGCTCTGAT GCCGCCGTGT TCCGGCTGTC   2580

AGCGCAGGGG CGCCCGGTTC TTTTTGTCAA GACCGACCTG TCCGGTGCCC TGAATGAACT   2640
```

```
GCAGGACGAG GCAGCGCGGC TATCGTGGCT GGCCACGACG GGCGTTCCTT GCGCAGCTGT    2700

GCTCGACGTT GTCACTGAAG CGGGAAGGGA CTGGCTGCTA TTGGGCGAAG TGCCGGGGCA    2760

GGATCTCCTG TCATCTCACC TTGCTCCTGC CGAGAAAGTA TCCATCATGG CTGATGCAAT    2820

GCGGCGGCTG CATACGCTTG ATCCGGCTAC CTGCCCATTC GACCACCAAG CGAAACATCG    2880

CATCGAGCGA GCACGTACTC GGATGGAAGC CGGTCTTGTC GATCAGGATG ATCTGGACGA    2940

AGAGCATCAG GGGCTCGCGC CAGCCGAACT GTTCGCCAGG CTCAAGGCGC GCATGCCCGA    3000

CGGCGAGGAT CTCGTCGTGA CCCATGGCGA TGCCTGCTTG CCGAATATCA TGGTGGAAAA    3060

TGGCCGCTTT TCTGGATTCA TCGACTGTGG CCGGCTGGGT GTGGCGGACC GCTATCAGGA    3120

CATAGCGTTG GCTACCCGTG ATATTGCTGA AGAGCTTGGC GGCGAATGGG CTGACCGCTT    3180

CCTCGTGCTT TACGGTATCG CCGCTCCCGA TTCGCAGCGC ATCGCCTTCT ATCGCCTTCT    3240

TGACGAGTTC TTCTGAGCGG GACTCTGGGG TTCGAAATGA CCGACCAAGC GACGCCCAAC    3300

CTGCCATCAC GAGATTTCGA TTCCACCGCC GCCTTCTATG AAAGGTTGGG CTTCGGAATC    3360

GTTTTCCGGG ACGCCGGCTG GATGATCCTC CAGCGCGGGG ATCTCATGCT GGAGTTCTTC    3420

GCCCACCCCC TGCTTTAATG AGATATGCGA GACGCCTATG ATCGCATGAT ATTTGCTTTC    3480

AATTCTGTTG TGCACGTTGT AAAAAACCTG AGCATGTGTA GCTCAGATCC TTACCGCCGG    3540

TTTCGGTTCA TTCAATGAA TATATCACCC GTTACTATCG TATTTTTATG AATAATATTC    3600

TCCGTTCAAT TTACTGATTG TACCCTACTA CTTATATGTA CAATATTAAA ATGAAAACAA    3660

TATATTGTGC TGAATAGGTT TATAGCGACA TCTATGATAG AGCGCCACAA TAACAAACAA    3720

TTGCGTTTTA TTATTACAAA TCCAATTTTA AAAAAGCGG CAGAACCGGT CAAACCTAAA    3780

AGACTGATTA CATAAATCTT ATTCAAATTT CAAAAGGCCC CAGGGGCTAG TATCTACGAC    3840

ACACCGAGCG GCGAACTAAT AACGTTCACT GAAGGGAACT CCGGTTCCCC GCCGGCGCGC    3900

ATGGGTGAGA TTCCTTGAAG TTGAGTATTG GCCGTCCGCT CTACCGAAAG TTACGGGCAC    3960

CATTCAACCC GGTCCAGCAC GGCGGCCGGG TAACCGACTT GCTGCCCCGA GAATTATGCA    4020

GCATTTTTTT GGTGTATGTG GGCCCCAAAT GAAGTGCAGG TCAAACCTTG ACAGTGACGA    4080

CAAATCGTTG GGCGGGTCCA GGGCGAATTT TGCGACAACA TGTCGAGGCT CAGCAGGGGC    4140

TCGATCCCCT CGCGAGTTGG TTCAGCTGCT GCCTGAGGCT GGACGACCTC GCGGAGTTCT    4200

ACCGGCAGTG CAAATCCGTC GGCATCCAGG AAACCAGCAG CGGCTATCCG CGCATCCATG    4260

CCCCCGAACT GCAGGAGTGG GGAGGCACGA TGGCCGCTTT GGTCGACCTG CAGCCAAGCT    4320

TGGCGTAATC ATGGTCATAG CTGTTTCCTG TGTGAAATTG TTATCCGCTC ACAATTCCAC    4380

ACAACATACG AGCCGGAAGC ATAAAGTGTA AAGCCTGGGG TGCCTAATGA GTGAGCTAAC    4440

TCACATTAAT TGCGTTGCGC TCACTGCCCG CTTTCCAGTC GGGAAACCTG TCGTGCCAGC    4500

TGCATTAATG AATCGGCCAA CGCGCGGGGA GAGGCGGTTT GCGTATTGGG CGCTCTTCCG    4560

CTTCCTCGCT CACTGACTCG CTGCGCTCGG TCGTTCGGCT GCGGCGAGCG GTATCAGCTC    4620

ACTCAAAGGC GGTAATACGG TTATCCACAG AATCAGGGGA TAACGCAGGA AGAACATGT    4680

GAGCAAAAGG CCAGCAAAAG GCCAGGAACC GTAAAAAGGC CGCGTTGCTG GCGTTTTTCC    4740

ATAGGCTCCG CCCCCCTGAC GAGCATCACA AAAATCGACG CTCAAGTCAG AGGTGGCGAA    4800

ACCCGACAGG ACTATAAAGA TACCAGGCGT TTCCCCCTGG AAGCTCCCTC GTGCGCTCTC    4860

CTGTTCCGAC CCTGCCGCTT ACCGGATACC TGTCCGCCTT TCTCCCTTCG GAAGCGTGG    4920

CGCTTTCTCA ATGCTCACGC TGTAGGTATC TCAGTTCGGT GTAGGTCGTT CGCTCCAAGC    4980

TGGGCTGTGT GCACGAACCC CCCGTTCAGC CCGACCGCTG CGCCTTATCC GGTAACTATC    5040
```

-continued

```
GTCTTGAGTC CAACCCGGTA AGACACGACT TATCGCCACT GGCAGCAGCC ACTGGTAACA    5100

GGATTAGCAG AGCGAGGTAT GTAGGCGGTG CTACAGAGTT CTTGAAGTGG TGGCCTAACT    5160

ACGGCTACAC TAGAAGGACA GTATTTGGTA TCTGCGCTCT GCTGAAGCCA GTTACCTTCG    5220

GAAAAAGAGT TGGTAGCTCT TGATCCGGCA ACAAACCAC CGCTGGTAGC GGTGGTTTTT    5280

TTGTTTGCAA GCAGCAGATT ACGCGCAGAA AAAAGGATC TCAAGAAGAT CCTTTGATCT    5340

TTTCTACGGG GTCTGACGCT CAGTGGAACG AAAACTCACG TTAAGGGATT TTGGTCATGA    5400

GATTATCAAA AAGGATCTTC ACCTAGATCC TTTTAAATTA AAAATGAAGT TTTAAATCAA    5460

TCTAAAGTAT ATATGAGTAA ACTTGGTCTG ACAGTTACCA ATGCTTAATC AGTGAGGCAC    5520

CTATCTCAGC GATCTGTCTA TTTCGTTCAT CCATAGTTGC CTGACTCCCC GTCGTGTAGA    5580

TAACTACGAT ACGGGAGGGC TTACCATCTG GCCCCAGTGC TGCAATGATA CCGCGAGACC    5640

CACGCTCACC GGCTCCAGAT TTATCAGCAA TAAACCAGCC AGCCGGAAGG GCCGAGCGCA    5700

GAAGTGGTCC TGCAACTTTA TCCGCCTCCA TCCAGTCTAT TAATTGTTGC CGGGAAGCTA    5760

GAGTAAGTAG TTCGCCAGTT AATAGTTTGC GCAACGTTGT TGCCATTGCT ACAGGCATCG    5820

TGGTGTCACG CTCGTCGTTT GGTATGGCTT CATTCAGCTC CGGTTCCCAA CGATCAAGGC    5880

GAGTTACATG ATCCCCCATG TTGTGCAAAA AAGCGGTTAG CTCCTTCGGT CCTCCGATCG    5940

TTGTCAGAAG TAAGTTGGCC GCAGTGTTAT CACTCATGGT TATGGCAGCA CTGCATAATT    6000

CTCTTACTGT CATGCCATCC GTAAGATGCT TTTCTGTGAC TGGTGAGTAC TCAACCAAGT    6060

CATTCTGAGA ATAGTGTATG CGGCGACCGA GTTGCTCTTG CCCGGCGTCA ATACGGGATA    6120

ATACCGCGCC ACATAGCAGA ACTTTAAAAG TGCTCATCAT TGGAAAACGT TCTTCGGGGC    6180

GAAAACTCTC AAGGATCTTA CCGCTGTTGA GATCCAGTTC GATGTAACCC ACTCGTGCAC    6240

CCAACTGATC TTCAGCATCT TTTACTTTCA CCAGCGTTTC TGGGTGAGCA AAAACAGGAA    6300

GGCAAAATGC CGCAAAAAAG GGAATAAGGG CGACACGGAA ATGTTGAATA CTCATACTCT    6360

TCCTTTTTCA ATATTATTGA AGCATTTATC AGGGTTATTG TCTCATGAGC GGATACATAT    6420

TTGAATGTAT TTAGAAAAAT AAACAAATAG GGGTTCCGCG CACATTTCCC CGAAAAGTGC    6480

CACCTGACGT CTAAGAAACC ATTATTATCA TGACATTAAC CTATAAAAAT AGGCGTATCA    6540

CGAGGCCCTT TCGTC                                                     6555
```

(2) INFORMATION FOR SEQ ID NO: 3:

(i) SEQUENCE CHARACTERISTICS:
    (A) LENGTH: 5620 base pairs
    (B) TYPE: nucleic acid
    (C) STRANDEDNESS: double
    (D) TOPOLOGY: circular (ii) MOLECULE TYPE: DNA (genomic)

(iii) HYPOTHETICAL: NO (iii) ANTI-SENSE: NO (vi) ORIGINAL SOURCE:
    (A) ORGANISM: plasmid pVE108 (replicable in E.coli)

(ix) FEATURE:
    (A) NAME/KEY: -
    (B) LOCATION: 1..395
    (D) OTHER INFORMATION: /label= pUC18
      /note= "pUC18 derived sequence"

(ix) FEATURE:
    (A) NAME/KEY: -
    (B) LOCATION: complement (396..802)
    (D) OTHER INFORMATION: /label= 3'nos

```
        /note= "3' regulatory sequence containing the
        polyadenylation site derived from the nopaline
        synthase gene from Agrobacterium T-DNA"

(ix) FEATURE:
     (A) NAME/KEY: -
     (B) LOCATION: complement (803..1138)
     (D) OTHER INFORMATION: /label= barnase
         /note= "coding region of the barnase gene of
         Bacillus amyloliquefaciens"

(ix) FEATURE:
     (A) NAME/KEY: -
     (B) LOCATION: complement (1139..1683)
     (D) OTHER INFORMATION: /label= TA29
         /note= "sequence derived from tapetum specific
         promoter of Nicotiana tabacum"

(ix) FEATURE:
     (A) NAME/KEY: -
     (B) LOCATION: 1684..2516
     (D) OTHER INFORMATION: /label= 35S3
         /note= ""35S3" promoter sequence derived from
         cauliflower mosaic virus isolate CabbB-JI"

(ix) FEATURE:
     (A) NAME/KEY: -
     (B) LOCATION: 2517..3068
     (D) OTHER INFORMATION: /label= bar
         /note= "coding sequence of phosphinotricin
         acetyltransferase gene"

(ix) FEATURE:
     (A) NAME/KEY: -
     (B) LOCATION: 3069..3356
     (D) OTHER INFORMATION: /label= 3'nos
         /note= "3' regulatory sequence containing the
         polyadenylation site derived from Agrobacterium
         T-DNA nopaline synthase gene"

(ix) FEATURE:
     (A) NAME/KEY: -
     (B) LOCATION: 3357..5620
     (D) OTHER INFORMATION: /label= pUC18
         /note= "pUC18 derived sequence"

(xi) SEQUENCE DESCRIPTION: SEQ ID NO: 3:

TCGCGCGTTT CGGTGATGAC GGTGAAAACC TCTGACACAT GCAGCTCCCG GAGACGGTCA      60

CAGCTTGTCT GTAAGCGGAT GCCGGGAGCA GACAAGCCCG TCAGGGCGCG TCAGCGGGTG     120

TTGGCGGGTG TCGGGCTGG CTTAACTATG CGGCATCAGA GCAGATTGTA CTGAGAGTGC      180

ACCATATGCG GTGTGAAATA CCGCACAGAT GCGTAAGGAG AAAATACCGC ATCAGGCGCC     240

ATTCGCCATT CAGGCTGCGC AACTGTTGGG AAGGGCGATC GGTGCGGGCC TCTTCGCTAT     300

TACGCCAGCT GGCGAAAGGG GGATGTGCTG CAAGGCGATT AAGTTGGGTA ACGCCAGGGT     360

TTTCCCAGTC ACGACGTTGT AAAACGACGG CCAGTGAATT CGAGCTCGGT ACCCGGGGAT     420

CTTCCCGATC TAGTAACATA GATGACACCG CGCGCGATAA TTTATCCTAG TTTGCGCGCT     480

ATATTTGTT TTCTATCGCG TATTAAATGT ATAATTGCGG GACTCTAATC ATAAAAACCC      540

ATCTCATAAA TAACGTCATG CATTACATGT TAATTATTAC ATGCTTAACG TAATTCAACA     600

GAAATTATAT GATAATCATC GCAAGACCGG CAACAGGATT CAATCTTAAG AAACTTTATT     660

GCCAAATGTT TGAACGATCT GCTTCGGATC CTCTAGAGNN NNCCGGAAAG TGAAATTGAC     720

CGATCAGAGT TTGAAGAAAA ATTTATTACA CACTTTATGT AAAGCTGAAA AAACGGCCT     780

CCGCAGGAAG CCGTTTTTTT CGTTATCTGA TTTTTGTAAA GGTCTGATAA TGGTCCGTTG     840

TTTTGTAAAT CAGCCAGTCG CTTGAGTAAA GAATCCGGTC TGAATTTCTG AAGCCTGATG     900

TATAGTTAAT ATCCGCTTCA CGCCATGTTC GTCCGCTTTT GCCCGGGAGT TTGCCTTCCC     960
```

```
TGTTTGAGAA GATGTCTCCG CCGATGCTTT TCCCCGGAGC GACGTCTGCA AGGTTCCCTT    1020

TTGATGCCAC CCAGCCGAGG GCTTGTGCTT CTGATTTTGT AATGTAATTA TCAGGTAGCT    1080

TATGATATGT CTGAAGATAA TCCGCAACCC CGTCAAACGT GTTGATAACC GGTACCATGG    1140

TAGCTAATTT CTTTAAGTAA AAACTTTGAT TTGAGTGATG ATGTTGTACT GTTACACTTG    1200

CACCACAAGG GCATATATAG AGCACAAGAC ATACACAACA ACTTGCAAAA CTAACTTTTG    1260

TTGGAGCATT TCGAGGAAAA TGGGGAGTAG CAGGCTAATC TGAGGGTAAC ATTAAGGTTT    1320

CATGTATTAA TTTGTTGCAA ACATGGACTT AGTGTGAGGA AAAAGTACCA AAATTTTGTC    1380

TCACCCTGAT TTCAGTTATG GAAATTACAT TATGAAGCTG TGCTAGAGAA GATGTTTATT    1440

CTAGTCCAGC CACCCACCTT ATGCAAGTCT GCTTTTAGCT TGATTCAAAA ACTGATTTAA    1500

TTTACATTGC TAAATGTGCA TACTTCGAGC CTATGTCGCT TTAATTCGAG TAGGATGTAT    1560

ATATTAGTAC ATAAAAAATC ATGTTTGAAT CATCTTTCAT AAAGTGACAA GTCAATTGTC    1620

CCTTCTTGTT TGGCACTATA TTCAATCTGT TAATGCAAAT TATCCAGTTA TACTTAGCTA    1680

GATCCTACGC AGCAGGTCTC ATCAAGACGA TCTACCCGAG TAACAATCTC CAGGAGATCA    1740

AATACCTTCC CAAGAAGGTT AAAGATGCAG TCAAAAGATT CAGGACTAAT TGCATCAAGA    1800

ACACAGAGAA AGACATATTT CTCAAGATCA GAAGTACTAT TCCAGTATGG ACGATTCAAG    1860

GCTTGCTTCA TAAACCAAGG CAAGTAATAG AGATTGGAGT CTCTAAAAAG GTAGTTCCTA    1920

CTGAATCTAA GGCCATGCAT GGAGTCTAAG ATTCAAATCG AGGATCTAAC AGAACTCGCC    1980

GTGAAGACTG GCGAACAGTT CATACAGAGT CTTTTACGAC TCAATGACAA GAAGAAAATC    2040

TTCGTCAACA TGGTGGAGCA CGACACTCTG GTCTACTCCA AAAATGTCAA AGATACAGTC    2100

TCAGAAGACC AAAGGGCTAT TGAGACTTTT CAACAAAGGA TAATTTCGGG AAACCTCCTC    2160

GGATTCCATT GCCCAGCTAT CTGTCACTTC ATCGAAAGGA CAGTAGAAAA GGAAGGTGGC    2220

TCCTACAAAT GCCATCATTG CGATAAAGGA AAGGCTATCA TTCAAGATGC CTCTGCCGAC    2280

AGTGGTCCCA AAGATGGACC CCCACCCACG AGGAGCATCG TGGAAAAAGA AGACGTTCCA    2340

ACCACGTCTT CAAAGCAAGT GGATTGATGT GACATCTCCA CTGACGTAAG GGATGACGCA    2400

CAATCCCACT ATCCTTCGCA AGACCCTTCC TCTATATAAG GAAGTTCATT TCATTTGGAG    2460

AGGACACGCT GAAATCACCA GTCTCTCTCT ATAAATCTAT CTCTCTCTCT ATAACCATGG    2520

ACCCAGAACG ACGCCCGGCC GACATCCGCC GTGCCACCGA GGCGGACATG CCGGCGGTCT    2580

GCACCATCGT CAACCACTAC ATCGAGACAA GCACGGTCAA CTTCCGTACC GAGCCGCAGG    2640

AACCGCAGGA GTGGACGGAC GACCTCGTCC GTCTGCGGGA GCGCTATCCC TGGCTCGTCG    2700

CCGAGGTGGA CGGCGAGGTC GCCGGCATCG CCTACGCGGG CCCCTGGAAG GCACGCAACG    2760

CCTACGACTG GACGGCCGAG TCGACCGTGT ACGTCTCCCC CCGCCACCAG CGGACGGGAC    2820

TGGGCTCCAC GCTCTACACC CACCTGCTGA AGTCCCTGGA GGCACAGGGC TTCAAGAGCG    2880

TGGTCGCTGT CATCGGGCTG CCCAACGACC CGAGCGTGCG CATGCACGAG GCGCTCGGAT    2940

ATGCCCCCCG CGGCATGCTG CGGGCGGCCG GCTTCAAGCA CGGGAACTGG CATGACGTGG    3000

GTTTCTGGCA GCTGGACTTC AGCCTGCCGG TACCGCCCCG TCCGGTCCTG CCCGTCACCG    3060

AGATCTGATC TCACGCGTCT AGGATCCGAA GCAGATCGTT CAAACATTTG GCAATAAAGT    3120

TTCTTAAGAT TGAATCCTGT TGCCGGTCTT GCGATGATTA TCATATAATT TCTGTTGAAT    3180

TACGTTAAGC ATGTAATAAT TAACATGTAA TGCATGACGT TATTTATGAG ATGGGTTTTT    3240

ATGATTAGAG TCCCGCAATT ATACATTTAA TACGCGATAG AAAACAAAAT ATAGCGCGCA    3300

AACTAGGATA AATTATCGCG CGCGGTGTCA TCTATGTTAC TAGATCGGGA AGATCCTCTA    3360
```

```
GAGTCGACCT GCAGGCATGC AAGCTTGGCG TAATCATGGT CATAGCTGTT TCCTGTGTGA    3420

AATTGTTATC CGCTCACAAT TCCACACAAC ATACGAGCCG GAAGCATAAA GTGTAAAGCC    3480

TGGGGTGCCT AATGAGTGAG CTAACTCACA TTAATTGCGT TGCGCTCACT GCCCGCTTTC    3540

CAGTCGGGAA ACCTGTCGTG CCAGCTGCAT TAATGAATCG GCCAACGCGC GGGGAGAGGC    3600

GGTTTGCGTA TTGGGCGCTC TTCCGCTTCC TCGCTCACTG ACTCGCTGCG CTCGGTCGTT    3660

CGGCTGCGGC GAGCGGTATC AGCTCACTCA AAGGCGGTAA TACGGTTATC CACAGAATCA    3720

GGGGATAACG CAGGAAAGAA CATGTGAGCA AAAGGCCAGC AAAAGGCCAG GAACCGTAAA    3780

AAGGCCGCGT TGCTGGCGTT TTTCCATAGG CTCCGCCCCC CTGACGAGCA TCACAAAAAT    3840

CGACGCTCAA GTCAGAGGTG GCGAAACCCG ACAGGACTAT AAAGATACCA GGCGTTTCCC    3900

CCTGGAAGCT CCCTCGTGCG CTCTCCTGTT CCGACCCTGC CGCTTACCGG ATACCTGTCC    3960

GCCTTTCTCC CTTCGGGAAG CGTGGCGCTT TCTCAATGCT CACGCTGTAG GTATCTCAGT    4020

TCGGTGTAGG TCGTTCGCTC CAAGCTGGGC TGTGTGCACG AACCCCCCGT TCAGCCCGAC    4080

CGCTGCGCCT TATCCGGTAA CTATCGTCTT GAGTCCAACC CGGTAAGACA CGACTTATCG    4140

CCACTGGCAG CAGCCACTGG TAACAGGATT AGCAGAGCGA GGTATGTAGG CGGTGCTACA    4200

GAGTTCTTGA AGTGGTGGCC TAACTACGGC TACACTAGAA GGACAGTATT TGGTATCTGC    4260

GCTCTGCTGA AGCCAGTTAC CTTCGGAAAA AGAGTTGGTA GCTCTTGATC CGGCAAACAA    4320

ACCACCGCTG GTAGCGGTGG TTTTTTTGTT TGCAAGCAGC AGATTACGCG CAGAAAAAAA    4380

GGATCTCAAG AAGATCCTTT GATCTTTTCT ACGGGGTCTG ACGCTCAGTG GAACGAAAAC    4440

TCACGTTAAG GGATTTTGGT CATGAGATTA TCAAAAAGGA TCTTCACCTA GATCCTTTTA    4500

AATTAAAAAT GAAGTTTTAA ATCAATCTAA AGTATATATG AGTAAACTTG GTCTGACAGT    4560

TACCAATGCT TAATCAGTGA GGCACCTATC TCAGCGATCT GTCTATTTCG TTCATCCATA    4620

GTTGCCTGAC TCCCCGTCGT GTAGATAACT ACGATACGGG AGGGCTTACC ATCTGGCCCC    4680

AGTGCTGCAA TGATACCGCG AGACCCACGC TCACCGGCTC CAGATTTATC AGCAATAAAC    4740

CAGCCAGCCG GAAGGGCCGA GCGCAGAAGT GGTCCTGCAA CTTTATCCGC CTCCATCCAG    4800

TCTATTAATT GTTGCCGGGA AGCTAGAGTA AGTAGTTCGC CAGTTAATAG TTTGCGCAAC    4860

GTTGTTGCCA TTGCTACAGG CATCGTGGTG TCACGCTCGT CGTTTGGTAT GGCTTCATTC    4920

AGCTCCGGTT CCCAACGATC AAGGCGAGTT ACATGATCCC CCATGTTGTG CAAAAAAGCG    4980

GTTAGCTCCT TCGGTCCTCC GATCGTTGTC AGAAGTAAGT TGGCCGCAGT GTTATCACTC    5040

ATGGTTATGG CAGCACTGCA TAATTCTCTT ACTGTCATGC CATCCGTAAG ATGCTTTTCT    5100

GTGACTGGTG AGTACTCAAC CAAGTCATTC TGAGAATAGT GTATGCGGCG ACCGAGTTGC    5160

TCTTGCCCGG CGTCAATACG GGATAATACC GCGCCACATA GCAGAACTTT AAAAGTGCTC    5220

ATCATTGGAA AACGTTCTTC GGGGCGAAAA CTCTCAAGGA TCTTACCGCT GTTGAGATCC    5280

AGTTCGATGT AACCCACTCG TGCACCCAAC TGATCTTCAG CATCTTTTAC TTTCACCAGC    5340

GTTTCTGGGT GAGCAAAAAC AGGAAGGCAA AATGCCGCAA AAAAGGGAAT AAGGGCGACA    5400

CGGAAATGTT GAATACTCAT ACTCTTCCTT TTTCAATATT ATTGAAGCAT TTATCAGGGT    5460

TATTGTCTCA TGAGCGGATA CATATTTGAA TGTATTTAGA AAAATAAACA AATAGGGGTT    5520

CCGCGCACAT TTCCCCGAAA AGTGCCACCT GACGTCTAAG AAACCATTAT TATCATGACA    5580

TTAACCTATA AAAATAGGCG TATCACGAGG CCCTTTCGTC                         5620
```

(2) INFORMATION FOR SEQ ID NO: 4:

(i) SEQUENCE CHARACTERISTICS:

-continued

```
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: oligonucleotide MDB80

(ix) FEATURE:
        (A) NAME/KEY: -
        (B) LOCATION: 1..21
        (D) OTHER INFORMATION: /label= MDB80
            /note= "oligonucleotide designated as MDB80"

(xi) SEQUENCE DESCRIPTION: SEQ ID NO: 4:

CCGCTTGTCA GTGAATGTTG C                                      21

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: oligonucleotide MDB81

(ix) FEATURE:
        (A) NAME/KEY: -
        (B) LOCATION: 1..21
        (D) OTHER INFORMATION: /label= MDB81
            /note= "oligonucleotide designated as MDB81"

(xi) SEQUENCE DESCRIPTION: SEQ ID NO: 5:

CGAGGCCAT GGTTGCCGCC G                                       21

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: oligonucleotide MDB82

(ix) FEATURE:
        (A) NAME/KEY: -
        (B) LOCATION: 1..21
        (D) OTHER INFORMATION: /label= MDB82
            /note= "oligonucleotide designated as MDB82"

(xi) SEQUENCE DESCRIPTION: SEQ ID NO: 6:

ACGCATAGGC ATAGGATGAC G                                      21
```

(2) INFORMATION FOR SEQ ID NO: 7:

(i) SEQUENCE CHARACTERISTICS:
        (A) LENGTH: 3627 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Oryza sativa
        (B) STRAIN: Akihikari (ix) FEATURE:
        (A) NAME/KEY: -
        (B) LOCATION: 1..2845
        (D) OTHER INFORMATION: /label= PT72
            /note= "sequence comprising anther specific
            promoter PT72"

(ix) FEATURE:
        (A) NAME/KEY: -
        (B) LOCATION: 2733..2739
        (D) OTHER INFORMATION: /label= TATA
            /note= "TATA Box"

(ix) FEATURE:
        (A) NAME/KEY: -
        (B) LOCATION: 2765
        (D) OTHER INFORMATION: /note= "transcription initiation
            determined by primer extension"

(ix) FEATURE:
        (A) NAME/KEY: -
        (B) LOCATION: 2846..2848
        (D) OTHER INFORMATION: /label= ATG
            /note= "ATG start of translation of rice T72 gene"

(xi) SEQUENCE DESCRIPTION: SEQ ID NO: 7:

```
GACAATACAT CAAGTAAATC AAACATTACA AATCAGAACC TGTCTAAGAA TCCATCTTAA      60

TTCAGAAAAA AACTCAGATT AGATGTTCAT GCTTCCACCA GAAGCAGGAA TGTGCAACCT     120

ACACTTCCTG TAATTTCCAT ACTACAATGT CCCCACTGAC CACTGTGCCT GATGCTCTAT     180

TAGAATACCA CATCCTCCAT GGCTCCATGT AAATGCATAT AAATTTGACT CTTTAAATTA     240

GTAACTACAA TTTAAAATTT ATCGAACATT GTTCAAATTT ATAAACAGTT TCCCCAAATT     300

TAGATGCTCC CAAATGTACA CAGCTACTAG TAAAGCACCA TCCAGTTTCA CCTGAACAGG     360

ACTGACATAA ATGTGTGAAA AGGGGACGTC ATTCCCCCAA ATACAACTGA ACAATCCTCC     420

ATCAGAACAT TCATTTGATT GACATTACTC GGAGAGATAC AGCTCGCAGG CACACGAGAT     480

TCTTCTGCCT TTCCAATTGC CACGAACCCA CATGTCACAC GACCAACCAA AAAGAGAGAA     540

TTTTTCTTTG CACAAACAAA AAGTGAGATT TTTTTTTCGC CACAAAGGTG CGAACTTTCT     600

TCTCTCTCCC ACTTTCCAAT CAAGAAACGA AGCACTCAAA CCAAGAACAA ACCAAGGAAG     660

GAGAGATCGC TCCCTCTCCC AGAGCAAACG AAAGGAGAGA ACTCAGATGG ATGCGAACTA     720

CTACCTTGCC TCTTTCCCCG GAGAAGCAGC GAAGGAGAAG AGCGCGATGC CGCCGCCGCC     780

GCCGCCTCCG GCAACCTCCG GCTCCGGCGA GTCCGCCTCC TCCTCCTCTC TCACCTCTCT     840

CTTCCCAACC GTGTGGTGTT CGAGAAGCTT TTATGCGAGC GACGTGCAGT GGAAGCGGTT     900

GCTCCCAAGT CAAACTGATG GAGACCACCT ACTATCTTCC TCTTGTTTTC TTCTGCTTTT     960

CTTTTCTTTA TCTTTTTTCT TTCATTTTAT TTTGAGCGAT GAACTTGAGA ACAGTTTGGT    1020
```

```
TGTGGGTTAA ATTAAACGGT GCAGAATTGC AAAGCTACGT CCTTTTCGTC TGATTAAGGT    1080

GGTATCAGAA TCCTAATCTG TTAGCTCAGC ATTTGTTTTT GTGTGTTTAA TTGGCCATGA    1140

CATCAGATGG TTCAGACCGG TGGCAGGTCT TCATCGGAGA GGAGAATGAG AGCAATGCAA    1200

GTTGCAAACA ACAAACAGGT CCTTCCAAAC GGGTTGGTTT CATTCCACAG AACAGGATAG    1260

CAACCAGAGC ACAAACCGTT CAACAATATA TATATATATA TATATATATA TATATATATA    1320

TATATATATA TATATATATG ATTTAAAATT ATATTACTAT TTTTAGGATA CGGAACTCTT    1380

AACACATGAA AATCTAAACA TTTTCAACCA ATCAGAACTA CTAGAAAGAT AATCTAACTA    1440

CTTCAAAATT TAAAATTTGA CAAATAAAAT AACTAGTTTT TTCTAAAGCT ATCTTCACTG    1500

GACAACTTAT GAATATTTAT ATTTATGAAG CGAGTACTCT CCTAGTACAT ATTACATATA    1560

TATTCTTCTT CTCATGAAAA ATTAACTTCT CGCTATAAAT CCGAACATAT ATTATGCGTA    1620

GCAAGTTGTT TTTTTAACG GGTGGAGTAA TATTAGAGTA TTTAAATTCC TTCAAATTGC    1680

CATCCCTCTG GGACTTTGCT GCTGTTGTTC TTCCACGGTT GCTGTCAGTG TCACCCAGAT    1740

TTGCATCCTT TCCAGCTCGT AGCTACTGTT CTGCATGTAT TGGACTTGGA TTAAGATCAA    1800

ATGCAGTTGC TATTGTAACT GCACAATAGC AACTGCACAC AATCATGTCC ATTCGTTTTC    1860

AGATCCAACG GCTCTAGATG ACTGCTACAG TACATGCATA ATAGTACATC TCTGCTACAG    1920

TGTTTTTGCT GCAGTACCAC TTCATATCCT GGCCTTCCGT TCTAGATCAT GTGATGTACA    1980

TGTTTTTTTG AAACAACCCG CACAAGACAT TGATAGAGTA GGAAATGTGA TGTACATGTT    2040

AACGGCTTAA GTTACAGTTA CAATAACAAC TGCACAGGAT CTTGATCCAT GGACTTGTA     2100

TAATATCTCA TCTCGTCGTT CCATTATCGT GGTAACAGTT GGCAACTTGG CATCCAGTGC    2160

TGGAAACTAT GCCGTGTGTA CATCAGGATC GTCCTTTTTG TTCAGTTCCA AGATAGAACA    2220

AGTCCAAAAG ATGGCCGTAG TTTTTTTAGT CACAGTGGAA GCTGACATAG CCGTGGAATA    2280

AGTTCTGCAC AAAAGTTGCC ATTCGAGATC AACTACTGGT AGTAGTAGTC ATCTTCTACC    2340

ACTGCGAATA TTCGAAGGGA CACAAAAAGA TCAACGAGTA AATTAGTTCA CCGGAAGACG    2400

ACACATTATC ACCACAAAAA GACTAAAAAC AAAAAGAAAT TGCCAGGCCA AAAAAGGCAA    2460

AAAAGAAAAA AAAAGATGGC ACGAGGCCCA GGGCTACGGC CCATCTTGTC GCCGGCCCAA    2520

CCGCGCGCGC GAAACGCTCT CGTCGGCTCT CGGCTCGCCG CGACGCGATG GAGAGTTCGC    2580

GCCGCGGCGC GCGCGCGCGT TCGGTGGCTC ACACGCTTGC GCCCTCGTCC TCCCGGCCGG    2640

CGCGGGCGCC GACCGCGCGT CCGCCGCATG CGCGCGGCGT AGGTGAGCAA CGCGGGCCTC    2700

GCCGCGCGCG CTCCCCTCCT TCGATCCCCT CCTATAAATC GAGCTCGCGT CGCGTATCGC    2760

CACCACCACC ACGACACACA CGCACGCACC GTGCAGGCAT CGACGACGAG CGAGAGCCCC    2820

TCGGCGGCAG AAGACACTCA CGGCGATGGC GGTGACGAGG ACGGCGCTGC TGGTGGTGTT    2880

GGTAGCGGGG GCGATGACGA TGACGATGCG CGGGGCGGAG GCGCAGCAGC CGAGCTGCGC    2940

GGCGCAGCTC ACGCAGCTGG CGCCGTGCGC GCGAGTCGGC GTGGCGCCGG CGCCGGGGCA    3000

GCCGCTGCCG GCGCCCCCGG CGGAGTGCTG CTCGGCGCTG GGCGCCGTGT CGCACGACTG    3060

CGCCTGCGGC ACGCTCGACA TCATCAACAG CCTCCCCGCC AAGTGCGGCC TCCCGCGCGT    3120

CACCTGCCGT AAGAAAACGA ATAAAATCGA TTTGCTATCT ATCGATGATT GTGTTTTTGT    3180

AGACTAAACT AAACCCCTAT TAATAATCAA CTAACCGATG AACTGATCGT TGCAGAGTGA    3240

TGGAGATGGT GTGCCAAGGT AATTGCGTTT GCTCGTGCGA GGATGAGAAG AGAAGATTGA    3300

ATAAGATGTT TGATGGCAAC AAGTCATCAG GCGATCCGAT CCCTGCAGCT ATGAATGGGA    3360

GTATACGTAG TAGTGGTCTC GTTAGCATCT GTGTGTCGCA TATGCACGCC GTGCGTGCCG    3420
```

5,977,433

-continued

```
TGTCTGTCCT GCTTGCTCTG CTGATCGTTC AATGAACGAC AAATTAATCT AACTCTGGAG    3480

TGACAAGTCG TTCGAGATAT ACTAATACTA CCATGTGCAG GGTCTTTCAA CCAAGGTTCA    3540

TGTTTTCCAC GAAAGCCGAT TGAAACGAAA CCGCGAAATT TTGATGCGAG ATGAAAGCAG    3600

ATTCCGAGTG AAATTTTAAA TGGTTTT                                        3627
```

(2) INFORMATION FOR SEQ ID NO: 8:

(i) SEQUENCE CHARACTERISTICS:
  (A) LENGTH: 2370 base pairs
  (B) TYPE: nucleic acid
  (C) STRANDEDNESS: double
  (D) TOPOLOGY: linear (ii) MOLECULE TYPE: DNA (genomic)

(iii) HYPOTHETICAL: NO (iii) ANTI-SENSE: NO (vi) ORIGINAL SOURCE:
  (A) ORGANISM: Oryza sativa
  (B) STRAIN: Akihikari (ix) FEATURE:
  (A) NAME/KEY: -
  (B) LOCATION: 1..1808
  (D) OTHER INFORMATION: /label= PT42
   /note= "sequence comprising anther specific
   promoter PT42"

(ix) FEATURE:
  (A) NAME/KEY: -
  (B) LOCATION: 1748..1755
  (D) OTHER INFORMATION: /label= TATA
   /note= "TATA Box"

(ix) FEATURE:
  (A) NAME/KEY: -
  (B) LOCATION: 1780
  (D) OTHER INFORMATION: /note= "transcription initiation
   site determined by primer extension"

(ix) FEATURE:
  (A) NAME/KEY: -
  (B) LOCATION: 1809
  (D) OTHER INFORMATION: /label= ATG
   /note= "ATG start of translation of rice T42 gene"

(xi) SEQUENCE DESCRIPTION: SEQ ID NO: 8:

```
GGCCATCACT GTCGGGTGCT GCGCCATGGA CATCACCGTC TCCTTCCTGC GCCGCCGTCG     60

CCGGTGAGCT CCAAGGCCGA AGCCTTCTTC CCCTCACGCC ACTACCTCTC TCTTCCCCAA    120

TTCCGGCCAA CGCCGTCCGT TGCCACAGCG CCACCTCCAC GCCATCCCAG AGCCCCGTGC    180

CGTGCCACCG GGTTCGCCTC CATCTCCTCT TGCCAACGCC GACGCTCGTC GCGGCAGCCA    240

TGCGCTGTCA CCGATGAACA CCGCCGCGCC ACAGCCATGG CAGAGCACGG CCAGGGAGCC    300

ATGGCTGCTC TGCCTCCTCC TCCTTCTCTC ACATCTGGTT GCAGCCGGAC CTAGTCGGCT    360

TATACAAATG GCCCATGGGC AAAATTGTCT TTTATGAAAG TTTCTCTCAC CGTTTCAGTC    420

GGAAATAATA AATAATGGG AGGATTGTCC GCCAGCAAAT TACCATATTT TTTCGGTGTC     480

CAAGAGCAAA TACACGATCT TCGGGTGTTT CACAGCAAAG ACCACAATTT CTAAGTGTCC    540

TGTAACAAAT TTTGCCAATA AAAATTTAAA ACCAAAGGAG AAGACTGTAC ATGAAGAAAA    600

ACAAAGAGAA TGAAATTACA TAAGCTCAGG GGTTATAAAG TTGATTTATT TTTAGGATGA    660

AGGAAGTGTG TGAAAACAAT GGCCAATTGG GTGTCGGAAA ATATAACGTG CTTGCTAAAA    720

TGTCGTCCCC ATATCCTGTA GCTGATTATA GATAGACCCT GATGGTCAAG ATGCCCTGTA    780
```

-continued

```
CTGGATCGTG TTTCCATGCT TCATCTCCGC TTCTCTCAAG TACTCCCCGA ACTCACATAT    840

CTGGTGGGCT GGATCCACAG TAAGAAACAG TCAAACAACA CTCACTTCAT AGATAACCAA    900

TTGTTTAATT ATTCTTAGTC CCTTATCTTA TACTCCTAGT AAGTGCTTAA AAACTTGGTA    960

TAAATATCAA ATTTATCGTA CAATTACAAT ATAATTATAA CGTATACCAT GTAATTTTTA   1020

AAACTATTTT TAGATAAAAA AAATATGGTG ATGAGCAGCC GCAGCAGCGG ACGCCGAACC   1080

ACCTGCCGAA CATCACCAAG ATAGCGAGTC CTAAAAATTT TTAGTGTTCG TTTGCTGGGT   1140

TGGTAACTAA TTAAAAAAAA AGAGCGACTC ATTAGCTCAT AAATAATTAC GTATTAGCTA   1200

ATTTTTTTAA AAAATAAATT AATATAACTT ATAAAGCAGC TTTTGTATAA TTTTTTTTTT   1260

AAAAAAGTGT TGTTTAGCAG TTTTGGGAAG TGTGCCGAGG GAAAACGATG AGATGGGTTG   1320

GGGAAGGAGG GGGAAGAAGT GAAGAACACA GCAAATATAG GCAGCATCGT CCCGTACAGA   1380

TCAGGCTGCA ACCACGCCCC GCGGAGATAG TTAACGCGGC CCACGTTGTG CTATAGCCCG   1440

TCACTCTCGC GGGCCTCTCC AACCTCCAGT TTTTTTTCTA GCCCATCAGC TGATACGGGG   1500

CCTTCCCCCC ATGCAGGAGG ATGGCCCGCC ACGCGGTGTT TTGGGCCGTT CTCGCCGCGC   1560

GCGCCCGTGC CGATCCGGGA CTCATCCCAC GTGCCGCCTC GCCACCGCCG CCGCCGCCGC   1620

TGCTGCTCCG GCTGCCGGCT GGACCTTCAC GCTCACGCGC TCTCCCCTGC CCAACCACCA   1680

CGCAAACAAA CACGAAGTTC GCGCCGTCGA CCGGCTCCCC TCCTCCCCCG CGCGCATCGG   1740

ATCCCCCTAC ATAAACCCTC TCGCTCGCCA TCGCCATGGC AGCAACTCCC CTCCTCCACT   1800

AGACCACCAT GCACAGATCG ATGGCCTCTC AGGCGGTGGC GCCCCTCCTC CTCATCCTCA   1860

TGCTCGCGGC GGCGGCGGGG GGCGCGTCGG CGGCGGTGCA GTGCGGGCAG GTGATGCAGC   1920

TGATGGCGCC GTGCATGCCG TACCTCGCCG GCGCCCCCGG GATGACGCCC TACGGCATCT   1980

GCTGCGACAG CCTCGGCGTG CTCAACCGGA TGGCCCCGGC CCCCGCCGAC CGCGTCGCCG   2040

TCTGCAACTG CGTCAAGGAC GCCGCCGCCG GCTTCCCCGC CGTCGACTTC TCCCGCGCCT   2100

CCGCCCTCCC CGCCGCCTGC GGCCTCTCCA TCAGCTTCAC CATCGCCCCC AACATGGACT   2160

GCAACCAGTA AGTTCATTCA TTCTTTCTTA ACTCCAATTC AATTTATCCA TCACCTCGAC   2220

TTAAGCCTGA TTAAACTTAA CTTGTTCTTT GCATGCTTGC ACTATTGCAG GGTTACAGAG   2280

GAACTGAGAA TCTGAGAGCG TGAGGAATCG AGTTCATGTT GCATTTATCA TCAATCATCA   2340

TCGACTAGAT CAATAAATCG AGCAAAGCTT                                    2370
```

(2) INFORMATION FOR SEQ ID NO: 9:

(i) SEQUENCE CHARACTERISTICS:
        (A) LENGTH: 2407 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Oryza sativa
        (B) STRAIN: Akihikari (ix) FEATURE:
        (A) NAME/KEY: -
        (B) LOCATION: 1..2263
        (D) OTHER INFORMATION: /label= PE1
            /note= "sequence comprising anther specific
            promoter PE1"

(ix) FEATURE:
    (A) NAME/KEY: -
    (B) LOCATION: 2181..2187
    (D) OTHER INFORMATION: /label= TATA
        /note= "TATA Box"

(ix) FEATURE:
    (A) NAME/KEY: -
    (B) LOCATION: 2211
    (D) OTHER INFORMATION: /note= "transcription initiation
        site determined by primer extension"

(ix) FEATURE:
    (A) NAME/KEY: -
    (B) LOCATION: 2264..2266
    (D) OTHER INFORMATION: /label= ATG
        /note= "ATG start of translation of E1 gene"

(xi) SEQUENCE DESCRIPTION: SEQ ID NO: 9:

```
TGATAGTGAC ATACTCACAT GCTTTGTCAA TTCAAGTATC AGTTCTTTTC ATATTGATTT      60

CTTAGTTGAT GAAAGTATAC ATATTTCTTG CCATCAATTC TTTTAGTAGG TACATTTGGA     120

CACTAGTGGT CAGGGTTGAA CTCTTAACTG GAGTCTCATC TGATTTGCTT ATCTGAGACT     180

GGGTTTGTGC AAATCCTGTC ATGAGGCAAG GTGGACTGTC AGTCCATGAC ACTTTGCTAC     240

TTCTATTAAG TTCTCGAAAT CTTTTCCAGT GTATGTCCGT TCTCTTTCAA ATGAATTATT     300

TATATGTTCT GACAGCCTCG CGGTGTACAT TTCATTTAAC TTTTGTCTTC ACAGGGCCTC     360

TTGGTATTTT GTTGAGCAGA TTGGAATCAA CCTTCTTGTA GAACTTCTTG ATGTCGTCGC     420

TACCCTTTGC AACTAGATGG TCAACTTCTG TCTTATATCT TTGGTACAAC ACTGGCAAAG     480

TGTGCGCGCA CAAGAATCCT GTGAAGTAAG AAATACAAAC TTGTCATTGT GAAAGTTTAG     540

CTTTATATGA TCTTGACTCT AAATTGTTTC TCCTCAGATC CTTCTGTGTG ATTGTTTTAT     600

TAAAATTTAA TATTTATCTG GAATACCTAC CAATATATAG TAGACTTGTC AAGCTGCAAG     660

AACTTCCAAT CGCCGACAAT ACCAATAGAG ATCCAACCAC CTTAATATCA TAAACAATCT     720

GATTGTTAGT CCAGAACTAT ATTGAGTAGT GAACAACAAT AGCACATTAA CATTATGAGG     780

ATTATTGGCT AACTCTGCAA TTCAATATTC TGATGCGTCT AATCTGGTCA ATTTTAGCGC     840

TCCAGAAAGA ATTGCACAAT CCTTGGACAA TGTTGGCACT GGAACTGTTG CATGTTTTTA     900

CATCTCTTAT TAACGTAGCA AAGGAGTAGA TTATTATGTA CCAGGAGAAA TCTCTTCAGA     960

TCCTTTCCAC ATGCAATGTC GTAAAGAACA GATACAGTGT ACGTTAGTTT GTAATGGACG    1020

GTCAATGCCA TTTCTCTGAA GGCATGTTCA GAGATGATGA TTTCTGGGAT CCTTGGAGGG    1080

GCCCTGAAAT TCGGAAACAG TTAGTTGAGT TTTAGTACCT AATGTCTTGC GTTATACTAC    1140

GTGAAATGCC ATTTCTGTAA GCTGAGTTTT CTACCATCTC CACAGGAAAT AAAGCTAATA    1200

CCTGTCCAAG AGTGGTGCGG CATTTGACCA ATGAAGATC ACAAGCATGG CAAGAATGGC    1260

AATCTGGCAA AGGAGCGGAA TTATATTGTA TTCTACTACA TCGAACAGGA ACCATATCAA    1320

TGTTGCCCCA GCAAGGACCC CCGCAGATAA GTTCCTGTTC TTCCACAGCA GAATATCCGC    1380

AACTGCATAG CTCCCAACAA TGAAATCCAA ACCACATCG GCTCAGAGAG AAGTTATGAT    1440

AAAAGGCACT AATTCTGAAT AATTTCCTAG AAAGCGAATA ATAATAGCAC ACCTTGACCT    1500

CCACCAAGAA GCTTGTGGAT CGACTTGTGC CCATGAAATG GCATTCTGAC ATTCTGGTCA    1560

CTGTCAGAAT CTCTCGGAAA ATGAGGAGGC ATAGCTTCGT GTGTGTATGT GTGTGGGATA    1620

TTACGCTGCT AAAACTTTGT GTTTCTGATC GATCTGGTTA GAGAGCATCG TCTTTATAAG    1680

CACTTAAAAA TGGTAGTATA ATCTCTCAAG GAGCCTATAC TGCCAAGGAA AGGATAGCTT    1740

GGCCTGTGGG GATTGAGCCG TTGAAGGGAA CAAACGAATA CAGTTACCTT ACCAGATGTT    1800
```

```
TGCCACGACA TGGGCAACGT CATTGCTAGA CCAAGAAGGC AAGAAGCAAA GTTTAGCTGT      1860

CAAAAAGAT ATGCTAGAGG CTTTCCAGAA TATGTTCTAT CTCAGCCAGA CCAATGGGGG       1920

CAAAATTTAC TACTATTTGC CATACATTAA CCACGTAAAA GTCCTACACT CAACCTAACT      1980

GTTGAACGGT CCTGTTCTGG CCAACGGTGA GAATGCACCT AATGGACGGG ACAACACTTC      2040

TTTCACCGTG CTACTGCTAC ATCCTGTAGA CGGTGGACGC GTGAGGTGCT TTCGCCATGA      2100

CCGTCCTTGG TTGTTGCAGT CACTTGCGCA CGCTTGCACC GTGACTCACC TGCCACATTG      2160

CCCCCGCCGT CGCCGGCGCC TACAAAAGCC ACACACGCAC GCCGGCCACG ATAACCCATC      2220

CTAGCATCCC GGTGTCCAGC AAGAGATCCA TCAAGCCGTC GCGATGACGA CGAGGCCTTC      2280

TGTTTTTTCC ACCGTTGTCG CGGCGATCGC CATCGCCGCG CTGCTGAGCA GCCTCCTCCT      2340

CCTGCAGGCT ACCCCGGCCG CGGCCAGCGC GAGGGCCTCG AAGAAGGCTT CGTGCGACCT      2400

GATGCAG                                                               2407

(2) INFORMATION FOR SEQ ID NO: 10:

(i) SEQUENCE CHARACTERISTICS:
        (A) LENGTH: 2784 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Zea mays (ix) FEATURE:
        (A) NAME/KEY: -
        (B) LOCATION: 1..1179
        (D) OTHER INFORMATION: /label= PCA55
            /note= "region comprising the anther specific
            promoter and the leader sequence, PCA55"

(ix) FEATURE:
        (A) NAME/KEY: -
        (B) LOCATION: 1072
        (D) OTHER INFORMATION: /label= TATA
            /note= "TATA Box"

(ix) FEATURE:
        (A) NAME/KEY: -
        (B) LOCATION: 1180..1596
        (D) OTHER INFORMATION: /note= "presumed coding sequence of
            corn CA55 gene"

(xi) SEQUENCE DESCRIPTION: SEQ ID NO: 10:

TGGTATGCAT CAATAGAGCC GGAAGATGGT CTGGAGTAAG GACCTGGCAG TGTGATACGG        60

GAACTTGACA TCTGAATAGA TATTCTCCCT TGTCCCTCTG GTAAAAAAAA CTGTTGTCAC       120

ATTTGCCTTC GCTGTGACTT GGATGTATCA TGTATATCTT TGACCATTGA TATCTTGGTT       180

AATCAGACGG TGCATTACAA TCATGGCCTC ATTCATATAG GGTTTAGGGT TACCACGATT       240

GGTTTGCATA AGTAGTACCC CTCCGTTTCA AATTATGTCG TATTTTGATT TTTTAGATAC       300

ACTTTTTATA TAATTTTTTA TTTTAAATTA GGTGTTTTAT ATAATACGTA TCTAAGTGTA       360

TAATAAAATA TATGTATCTA AAAGCTGTAA TTTAGTATAA ATTAGAATGG TGTATATCTT       420

CAATGTATGA CAAATAATTT GAAATGGAGG AGGGTATGAA AAGCCAAAAC CTCCTAGAAT       480

ATGGAATGGA GGGAATACAT ACAAATTCTT TGCTTCAGTT AAAAGAAACG AGAAAAGGAG       540

GGGAATGGGG AATCGTACTT CAGTTTTTAC GAGTTTTCAT CAAACATGTA TGCACGTCTT       600
```

```
CCCTTGGTTG ATGCATCTTT TTGGCAAATC TTCGTTTAAT TGCGGCTTCT TTTTTATACC      660

GTTCGAAGGT TTTCGTCGTC AATGCTGAAA CTCCACTTTC ACCACCTTCG GTTGCATCTG      720

CTTGCTTTCA ATTCACCTCT AATTAGTCCA AGTGTTTCAT TGGACGAAGG TCCAAGTCCT      780

TCAGATCATC TCAATTTTCT TTGATCTGAA ACAACAATTT AAAACTGATT TTGTTACCTT      840

GACCTGTCGA AGACCTTCGA ACGAACGGTA CTGTAAAAAT ACTGTACCTC AGATTTGTGA      900

TTTCAATTCG ATTCGGGTCT CCTGGCTGGA TGAAACCAAT GCGAGAGAAG AAGAAAAAAT      960

GTTGCATTAC GCTCACTCGA TCGGTTACGA GCACGTAGTT GGCGCCTGTC ACCCAACCAA     1020

ACCAGTAGTT GAGGCACGCC CTGTTTGCTC ACGATCACGA ACGTACAGCA CTATAAAACA     1080

CGCAGGGACT GGAAAGCGAG ATTTCACAGC TCAAAGCAGC CAAAACGCAG AAGCTGCACT     1140

GCATATACAG AAGATACATC GAGCTAACTA GCTGCAGCGA TGTCTCGCTC CTGCTGCGTC     1200

GCCGTGTCGG TGCTTCTCGC TGTCGCCGCG ACAGCCAGCG CCACCGCGCC GGCATGGCTG     1260

CACGAGGAGC AGCACCTCGA GGAGGCCATG GCCACGGGCC CGCTGGTCGC AGAGGGTGCG     1320

AGGGTGGCGC CCTCCGCGTC CACCTGGGCT GCCGACAAGG CGTCGCCGGC GAGGCCGAGC     1380

GGCGGCATGG CCACGCAGGG CGACGACCAG AGCTCGTCGG GCGGCAGTGG CAGCAGCGGT     1440

GAGCACGGCA AGGCGGAGGG CGAGAAGCAG GGCAAGAGCT GCCTCACCAA GGAGGAGTGC     1500

CACAAGAAGA AGATGATCTG TGGCAAGGGC TGCACGCTCT CGGCGCACAG CAAGTGCGCC     1560

GCCAAGTGCA CCAAGTCCTG TGTCCCCACC TGCTAGGAGC CGAGGCCGGA GCTTGCCGGC     1620

GGCGAGACCT CGATCGATCG AGTGCTTCAC TTCACTTCTT TGTTATAGTT CTTGTGTGTT     1680

GCCGTTGCGT TGCGTTGCGT AGACGAAGGG AATAAGGAAG GGTAATTGGA TTACCTGTTC     1740

CAGATCTCTG TGTAAGCGTG TTGTCGTGAC AAGTCTTTTG ATCCAGAGCG AGGGATGGAT     1800

AGATCGCGCT CGCAGTTTTA ATTGCAATGC TAGTTCAATA TGTGTGCATC ATGTTGGCAA     1860

CTACATAGTC CAGATTCAAA CCGAGATCGC TGTTTAGCAT GCCAGCACAA TAATAACGGT     1920

ACAATCATAT TATATTTTAT ACAAATGCAC AATTTATCTC TAGAGATGTC AATGGGAAAT     1980

TCCTCATCGG GTTATATCAT CTCAGACTCA TCCCCATCAT ATTTGATTCA TCCTCATACT     2040

CATCCTCATA TCTATCATGA GTGCAAAACT CATTTCATAC CCATCTCTAT TTTGGTTTAG     2100

GGTCTCCATC CCTAATTAAG GGATAACTAG TACTAACAAC TAGCACAAAC TATCTAGATT     2160

TCAGATATCA CCACATTGAC AAACAATCAT CCATGAACTA TGATCCATTC ATCCATCCAT     2220

CAAAAAATAA ATCGGTATTT CGAGAACGAT AGAAGAAATG AAGTCGGCTC ACCTTTCTTG     2280

GTCACCATTT GAGTTTGTTG GTGCCTGAGA ATCCATGGTC GTCATCGTCG TCCTAGGGAT     2340

CGGCGGTGCT CCTCGTTGTT GGTAAAGTCG CCAGTGTGTA GTGCTAGCGC AACTGTCCAG     2400

GCGTGCAACG GTTGGCCGGC TGGAAAGGGC ATAGCGTATG GCTGGTTATT TTTAGGGTTT     2460

TGTTTTTTTA CTAATCTGCT AGTTGCCTTG CCATGTTGTC TTATTGGGCT AGGATCTAGG     2520

GCTTGTTACG CTGCTGTGTT GGGCTTGGTG TCCGGTTCAG CCTCAACTCA TTCATACAAA     2580

TCAGATTCAT ACAAAACAGG TATACACGTA TGAAATATCC ATGGATAATC AGGTTCGAAT     2640

TATTGTCCCC TAAACCCATA CACGTTTACC CAATGGATGG ATATTTTGTC TCATATCCAT     2700

ACACATGAGA CGATTTTTGT CCCATACCTG TGCTCTAATA GGAGAATTTC TCTCGGGATA     2760

GCGAGTATCG GATCCTCTAG AGTC                                          2784
```

(2) INFORMATION FOR SEQ ID NO: 11:

(i) SEQUENCE CHARACTERISTICS:
        (A) LENGTH: 24 base pairs

```
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iii) ANTI-SENSE: NO (vi) ORIGINAL SOURCE:
           (A) ORGANISM: oligonucleotide Zm13Oli2

(ix) FEATURE:
           (A) NAME/KEY: -
           (B) LOCATION: 1..24
           (D) OTHER INFORMATION: /label= Zm13Oli2
               /note= "oligonucleotide designated as Zm13Oli2"

(xi) SEQUENCE DESCRIPTION: SEQ ID NO: 11:

GTGGATTGAA CGGGACTGAG TTGG                                              24

(2) INFORMATION FOR SEQ ID NO: 12:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iii) ANTI-SENSE: NO (vi) ORIGINAL SOURCE:
           (A) ORGANISM: oligonucleotide Zm13Oli1

(ix) FEATURE:
           (A) NAME/KEY: -
           (B) LOCATION: 1..25
           (D) OTHER INFORMATION: /label= Zm13Oli1
               /note= "oligonucleotide designated as Zm13Oli1"

(xi) SEQUENCE DESCRIPTION: SEQ ID NO: 12:

AAGTCTCCAA GACTTTGGTT ATTCC                                             25

(2) INFORMATION FOR SEQ ID NO: 13:

(i) SEQUENCE CHARACTERISTICS:
           (A) LENGTH: 31 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iii) ANTI-SENSE: NO (vi) ORIGINAL SOURCE:
           (A) ORGANISM: Oligonucleotide Zm13Oli5

(ix) FEATURE:
           (A) NAME/KEY: -
           (B) LOCATION: 1..31
           (D) OTHER INFORMATION: /label= Zm13Oli5
               /note= "oligonucleotide designated as Zm13Oli5"

(xi) SEQUENCE DESCRIPTION: SEQ ID NO: 13:

GGATCCATGG TTGCCGCCGG GTGAATGTAC G                                      31
```

(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: oligonucleotide BXOL2

(ix) FEATURE:
        (A) NAME/KEY: -
        (B) LOCATION: 1..24
        (D) OTHER INFORMATION: /label= BXOL2
            /note= "oligonucleotide designated as BXOL2"

(xi) SEQUENCE DESCRIPTION: SEQ ID NO: 14:

ACGGAAAACC TGAAGCACAC TCTC                                  24

(2) INFORMATION FOR SEQ ID NO: 15:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: oligonucleotide TA29SBXOL2

(ix) FEATURE:
        (A) NAME/KEY: -
        (B) LOCATION: 1..49
        (D) OTHER INFORMATION: /label= TA29SBXOL2
            /note= "oligonucleotide designated as TA29SBXOL2"

(xi) SEQUENCE DESCRIPTION: SEQ ID NO: 15:

GTTTTTACTT AAAGAAATTA GCTACCATGA AAAAAGCAGT CATTAACGG          49

(2) INFORMATION FOR SEQ ID NO: 16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: oligonucleotide PTA29OL5

(ix) FEATURE:
        (A) NAME/KEY: -
        (B) LOCATION: 1..27
        (D) OTHER INFORMATION: /label= PTA29OL5
            /note= "oligonucleotide designated as PTA29OL5"

(xi) SEQUENCE DESCRIPTION: SEQ ID NO: 16:

TGGCCATAAC TGAAATCAGG GTGAGAC                      27

(2) INFORMATION FOR SEQ ID NO: 17:

(i) SEQUENCE CHARACTERISTICS:
        (A) LENGTH: 4808 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: EcoRI-HindIII fragment of plasmid pTS218

(ix) FEATURE:
        (A) NAME/KEY: -
        (B) LOCATION: complement (18..401)
        (D) OTHER INFORMATION: /label= 3'nos
            /note= "3' regulatory sequence containing the
            polyadenylation site derived from Agrobacterium
            T-DNA nopaline synthase gene"

(ix) FEATURE:
        (A) NAME/KEY: -
        (B) LOCATION: complement (402..737)
        (D) OTHER INFORMATION: /label= barnase
            /note= "coding region of the barnase gene of
            Bacillus amyloliquefaciens"

(ix) FEATURE:
        (A) NAME/KEY: -
        (B) LOCATION: complement (738..1944)
        (D) OTHER INFORMATION: /label= PZM13
            /note= "promoter region of the Zm13 gene of Zea
            mays"

(ix) FEATURE:
        (A) NAME/KEY: -
        (B) LOCATION: complement (1945..2281)
        (D) OTHER INFORMATION: /label= 3'nos (ix) FEATURE:
        (A) NAME/KEY: -
        (B) LOCATION: complement (2282..2554)
        (D) OTHER INFORMATION: /label= barstar
            /note= "coding region of the barstar gene of
            Bacillus amyloliquefaciens"

(ix) FEATURE:
        (A) NAME/KEY: -
        (B) LOCATION: complement (2555..3099)
        (D) OTHER INFORMATION: /label= PTA29
            /note= "promoter region of the TA29 gene of
            Nicotiana tabacum"

(ix) FEATURE:
        (A) NAME/KEY: -
        (B) LOCATION: 3100..3932
        (D) OTHER INFORMATION: /label= 35S3
            /note= ""35S3" promoter sequence derived from
            cauliflower mosaic virus isolate CabbB-JI"

(ix) FEATURE:
        (A) NAME/KEY: -
        (B) LOCATION: 3933..4484
        (D) OTHER INFORMATION: /label= bar
            /note= "coding region of the phosphinothricin
            acetyltransferase gene"

(ix) FEATURE:
        (A) NAME/KEY: -
        (B) LOCATION: 4485..4763
        (D) OTHER INFORMATION: /label= 3'nos (ix) FEATURE:
    (A) NAME/KEY: -
    (B) LOCATION: 2333..2356
    (D) OTHER INFORMATION: /label= BXOL2
        /note= "region corresponding to oligonucleotide
        BXOL2"

(ix) FEATURE:
    (A) NAME/KEY: -
    (B) LOCATION: complement (2538..2586)
    (D) OTHER INFORMATION: /label= TA29SBXOL2
        /note= "region complementary to oligonucleotide
        TA29SBXOL2"

(ix) FEATURE:
    (A) NAME/KEY: -
    (B) LOCATION: complement (2800..2823)
    (D) OTHER INFORMATION: /label= PTA29OL5
        /note= "region complementary to part of
        oligonucleotide PTA29OL5"

(xi) SEQUENCE DESCRIPTION: SEQ ID NO: 17:

```
GAATTCGAGC TCGGTACCCG GGGATCTTCC CGATCTAGTA ACATAGATGA CACCGCGCGC      60

GATAATTTAT CCTAGTTTGC GCGCTATATT TTGTTTTCTA TCGCGTATTA AATGTATAAT     120

TGCGGGACTC TAATCATAAA AACCCATCTC ATAAATAACG TCATGCATTA CATGTTAATT     180

ATTACATGCT TAACGTAATT CAACAGAAAT TATATGATAA TCATCGCAAG ACCGGCAACA     240

GGATTCAATC TTAAGAAACT TTATTGCCAA ATGTTTGAAC GATCTGCTTC GGATCCTCTA     300

GAGNNNNCCG GAAAGTGAAA TTGACCGATC AGAGTTTGAA GAAAAATTTA TTACACACTT     360

TATGTAAAGC TGAAAAAAAC GGCCTCCGCA GGAAGCCGTT TTTTTCGTTA TCTGATTTTT     420

GTAAAGGTCT GATAATGGTC CGTTGTTTTG TAAATCAGCC AGTCGCTTGA GTAAAGAATC     480

CGGTCTGAAT TTCTGAAGCC TGATGTATAG TTAATATCCG CTTCACGCCA TGTTCGTCCG     540

CTTTTGCCCG GGAGTTTGCC TTCCCTGTTT GAGAAGATGT CTCCGCCGAT GCTTTTCCCC     600

GGAGCGACGT CTGCAAGGTT CCCTTTTGAT GCCACCCAGC CGAGGGCTTG TGCTTCTGAT     660

TTTGTAATGT AATTATCAGG TAGCTTATGA TATGTCTGAA GATAATCCGC AACCCCGTCA     720

AACGTGTTGA TAACCGGTAC CATGGTTGCC GCCGGGTGAA TGTACGTGTT TTCCCCTCCC     780

CCCTTGTGGA TGTCGGAGGA AAAGGGCGGG ACCTTTCCTT ATTATTTGTG TGAGGGAGGG     840

AGGGTGAGAC GAGGGTGGCA AATCTGGCCT GGTTTCGTAA CGCAGCCTGT GGTGTCCTTA     900

AATAATCTGC GAGACCCGAA GATTTGTCTG GCTGCCCGTA GAAATAGTGG CCGACGGCCA     960

GAAAGCCGTT TTGACCTAGT TTTGTGGCAT GGGGAGGTGA AAAATATGTC GAATTTGGTT    1020

GAGTTTTTCA GCGGTCCACA AAAGTTGGAT TTGCGACTTC TAATCTTCTA TGCTGCTATG    1080

TAAAACTAAA TAAGACGCGC TCAACAAAAC GGTATCAGTT AAATGTATCC ATAAGTGAAT    1140

AGTATATAGA ATCACTAAAT GGCAGCTTCT CATATTTAGC ATAGTACTTG GACAAATGTC    1200

ACGCAAGATG TATTATAAAA ACACATCGGT GTTGAGTGTT GATACAATAA AATCTCAATA    1260

GTTGTTTTAA TCTCAATCCA TGTGGATTGA ACGGGACTGA GTTGGTTTAA ATCCCTAGTA    1320

AGTCAAAATT ATTTCTAATT TTATCTAAAT CTCATCTAAT CCACGTGGAA TAGGAATAAC    1380

CAAACTGTTG GAGACTTGTT CTCAAGTGCT ATGAGTTAAG AACAAGGCAA CATAGAAAAT    1440

ATTAATCGTT AAGGTCCTTC GTCCTTCGAA GCATTATTTC CCTTAGGATA TAATGGTTTA    1500

CGGACGAAGG TTATGAAGGA CGTACCTTCA TAAATTCATT AAACAATGAC GAAGGATGAA    1560

ATATAAAGAA TATAAAAGAC AACATGAACA ATTATATATT ATTATTAGGT ACAAACAGAA    1620

ATATCGTTGA ATTACAAGTG TACCTTCAAT AGGAATGAGA TGACAGTACA AGCGTGACGC    1680
```

```
AAAAAGCGAA TGCCAAGTCA GCGTGAACAG TACGGGAATA CTGTTCACCT ATTTATAGGC    1740

ACGGGACGTA GCCTGTGCAA AATTACATTA ATGCCCTTTA CACTTAATAA TAAACCTATA    1800

GTAATCTGTT GAGGTCTAAA TAGCCTTTTC ATCTTTAAGT CGGTTTCAAC TGCTGCTGTC    1860

TTGCCGAAGC TTTCCTGCTT ACACCTTAGG CGCTTCACCA ACCTTCGTAT TATTCTGGTC    1920

TACTGTGATG CCTGACTTGA GTCCGAAGAT GGGGATCTTC CCGATCTAGT AACATAGATG    1980

ACACCGCGCG CGATAATTTA TCCTAGTTTG CGCGCTATAT TTTGTTTTCT ATCGCGTATT    2040

AAATGTATAA TTGCGGGACT CTAATCATAA AAACCCATCT CATAAATAAC GTCATGCATT    2100

ACATGTTAAT TATTACATGC TTAACGTAAT TCAACAGAAA TTATATGATA ATCATCGCAA    2160

GACCGGCAAC AGGATTCAAT CTTAAGAAAC TTTATTGCCA AATGTTTGAA CGATCTGCTT    2220

CGGATCCTCT AGACCAAGCT AGCTTGCGGG TTTGTGTTTC CATATTGTTC ATCTCCCATT    2280

GATCGTATTA AGAAAGTATG ATGGTGATGT CGCAGCCTTC CGCTTTCGCT TCACGGAAAA    2340

CCTGAAGCAC ACTCTCGGCG CCATTTTCAG TCAGCTGCTT GCTTTGTTCA AACTGCCTCC    2400

ATTCCAAAAC GAGCGGGTAC TCCACCCATC CGGTCAGACA ATCCCATAAA GCGTCCAGGT    2460

TTTCACCGTA GTATTCCGGA AGGGCAAGCT CCTTTTTCAA TGTCTGGTGG AGGTCGCTGA    2520

TACTTCTGAT TTGTTCCCCG TTAATGACTG CTTTTTTCAT GGTAGCTAAT TTCTTTAAGT    2580

AAAAACTTTG ATTTGAGTGA TGATGTTGTA CTGTTCACT  TGCACCACAA GGGCATATAT    2640

AGAGCACAAG ACATACACAA CAACTTGCAA AACTAACTTT TGTTGGAGCA TTTCGAGGAA    2700

AATGGGGAGT AGCAGGCTAA TCTGAGGGTA ACATTAAGGT TTCATGTATT AATTTGTTGC    2760

AAACATGGAC TTAGTGTGAG GAAAAAGTAC CAAAATTTTG TCTCACCCTG ATTTCAGTTA    2820

TGGAAATTAC ATTATGAAGC TGTGCTAGAG AAGATGTTTA TTCTAGTCCA GCCACCCACC    2880

TTATGCAAGT CTGCTTTTAG CTTGATTCAA AAACTGATTT AATTTACATT GCTAAATGTG    2940

CATACTTCGA GCCTATGTCG CTTTAATTCG AGTAGGATGT ATATATTAGT ACATAAAAAA    3000

TCATGTTTGA ATCATCTTTC ATAAAGTGAC AAGTCAATTG TCCCTTCTTG TTTGGCACTA    3060

TATTCAATCT GTTAATGCAA ATTATCCAGT TATACTTAGC TAGATCCTAC GCAGCAGGTC    3120

TCATCAAGAC GATCTACCCG AGTAACAATC TCCAGGAGAT CAAATACCTT CCCAAGAAGG    3180

TTAAAGATGC AGTCAAAAGA TTCAGGACTA ATTGCATCAA GAACACAGAG AAAGACATAT    3240

TTCTCAAGAT CAGAAGTACT ATTCCAGTAT GGACGATTCA AGGCTTGCTT CATAAACCAA    3300

GGCAAGTAAT AGAGATTGGA GTCTCTAAAA AGGTAGTTCC TACTGAATCT AAGGCCATGC    3360

ATGGAGTCTA AGATTCAAAT CGAGGATCTA ACAGAACTCG CCGTGAAGAC TGGCGAACAG    3420

TTCATACAGA GTCTTTTACG ACTCAATGAC AAGAAGAAAA TCTTCGTCAA CATGGTGGAG    3480

CACGACACTC TGGTCTACTC CAAAAATGTC AAAGATACAG TCTCAGAAGA CCAAAGGGCT    3540

ATTGAGACTT TCAACAAAG  GATAATTTCG GGAAACCTCC TCGGATTCCA TTGCCCAGCT    3600

ATCTGTCACT TCATCGAAAG GACAGTAGAA AAGGAAGGTG GCTCCTACAA ATGCCATCAT    3660

TGCGATAAAG GAAAGGCTAT CATTCAAGAT GCCTCTGCCG ACAGTGGTCC CAAAGATGGA    3720

CCCCCACCCA CGAGGAGCAT CGTGGAAAAA GAAGACGTTC CAACCACGTC TTCAAAGCAA    3780

GTGGATTGAT GTGACATCTC CACTGACGTA AGGGATGACG CACAATCCCA CTATCCTTCG    3840

CAAGACCCTT CCTCTATATA AGGAAGTTCA TTTCATTTGG AGAGGACACG CTGAAATCAC    3900

CAGTCTCTCT CTATAAATCT ATCTCTCTCT CTATAACCAT GGACCCAGAA CGACGCCCGG    3960

CCGACATCCG CCGTGCCACC GAGGCGGACA TGCCGGCGGT CTGCACCATC GTCAACCACT    4020

ACATCGAGAC AAGCACGGTC AACTTCCGTA CCGAGCCGCA GGAACCGCAG GAGTGGACGG    4080
```

-continued

| | | | | | |
|---|---|---|---|---|---|
| ACGACCTCGT | CCGTCTGCGG | GAGCGCTATC | CCTGGCTCGT | CGCCGAGGTG | GACGGCGAGG | 4140 |
| TCGCCGGCAT | CGCCTACGCG | GGCCCCTGGA | AGGCACGCAA | CGCCTACGAC | TGGACGGCCG | 4200 |
| AGTCGACCGT | GTACGTCTCC | CCCCGCCACC | AGCGGACGGG | ACTGGGCTCC | ACGCTCTACA | 4260 |
| CCCACCTGCT | GAAGTCCCTG | GAGGCACAGG | GCTTCAAGAG | CGTGGTCGCT | GTCATCGGGC | 4320 |
| TGCCCAACGA | CCCGAGCGTG | CGCATGCACG | AGGCGCTCGG | ATATGCCCCC | CGCGGCATGC | 4380 |
| TGCGGGCGGC | CGGCTTCAAG | CACGGGAACT | GGCATGACGT | GGGTTTCTGG | CAGCTGGACT | 4440 |
| TCAGCCTGCC | GGTACCGCCC | CGTCCGGTCC | TGCCCGTCAC | CGAGATCTGA | TCTCACGCGT | 4500 |
| CTAGGATCCG | AAGCAGATCG | TTCAAACATT | TGGCAATAAA | GTTTCTTAAG | ATTGAATCCT | 4560 |
| GTTGCCGGTC | TTGCGATGAT | TATCATATAA | TTTCTGTTGA | ATTACGTTAA | GCATGTAATA | 4620 |
| ATTAACATGT | AATGCATGAC | GTTATTTATG | AGATGGGTTT | TTATGATTAG | AGTCCCGCAA | 4680 |
| TTATACATTT | AATACGCGAT | AGAAAACAAA | ATATAGCGCG | CAAACTAGGA | TAAATTATCG | 4740 |
| CGCGCGGTGT | CATCTATGTT | ACTAGATCGG | GAAGATCCTC | TAGAGTCGAC | CTGCAGGCAT | 4800 |
| GCAAGCTT | | | | | | 4808 |

We claim:

1. A process for maintaining a male-sterile line of a plant species, said process comprising the steps of:
   1) crossing:
      a) a male-sterile line to be maintained comprising male-sterile parent plants which comprise a male-sterility gene at a first genetic locus wherein said male-sterility gene is homozygous at said first genetic locus; with
      b) a maintainer line comprising male-fertile parent plants which comprise said homozygous male-sterility gene at said first genetic locus, and which further comprise, at a second genetic locus which segregates independently from said first genetic locus, a foreign DNA comprising;
         (i) a restorer gene which, upon expression, inhibits or prevents the phenotypic expression of said male-sterility gene; and
         (ii) a pollen-lethality gene comprising, under the control of a first promoter that directs expression selectively in a microspore and/or a pollen cell of said male-fertile parent plants, a first DNA encoding a first protein or polypeptide which, when produced in said microspore or pollen cell of said male-fertile parent plants, significantly disrupts the metabolism, functioning or development of said microspore or pollen cell;
   wherein said foreign DNA is heterozygous at said second genetic locus; and
   2) harvesting seeds from said male-sterile parent plants, wherein said seeds grow into a new generation of male-sterile parent plants.

2. The process of claim 1, in which said first genetic locus in said male-sterile parent plants and said male-fertile parent plants is an endogenous locus comprising a recessive allele in homozygous condition, and in which said restorer gene is the dominant allele at said endogenous locus.

3. The process of claim 1, in which said first genetic locus in said male-sterile parent plants and said male-fertile parent plants is a foreign genetic locus and comprises a foreign male-sterility gene, which comprises a sterility DNA under the control of a sterility promoter directing expression selectively in specific stamen cells, and in which said restorer gene at said second genetic locus encodes a protein or polypeptide, which upon expression, inhibits or prevents the phenotypic expression of said male-sterility gene.

4. The process of claim 3, in which said sterility promoter directs expression in tapetum cells.

5. The process of claim 4, in which said sterility promoter is a TA29 promoter.

6. The process of claim 1, in which said first DNA encodes a ribonuclease.

7. The process of claim 6, in which said first DNA encodes a barnase.

8. The process of claim 1, in which said first promoter is a promoter of a zm13 gene from maize.

9. The process of any one of claims 1 to 3, in which said plant species is maize.

10. A male-fertile parent plant for use in maintaining a male-sterile line of a plant species comprising male-sterile parent plants which comprise a male-sterility gene at a first genetic locus, wherein said male-sterility gene is homozygous at said first genetic locus, wherein said male-fertile parent plant comprises said homozygous male-sterility gene at said first genetic locus and further comprises, at a second genetic locus which segregates independently from said first genetic locus, a foreign DNA comprising:
   i) a restorer gene which, upon expression, inhibits or prevents the phenotypic expression of said male-sterility gene; and
   ii) a pollen-lethality gene comprising, under the control of a first promoter that directs expression selectively in a microspore and/or a pollen cell of said male-fertile parent plant, a first DNA encoding a first protein or polypeptide which when produced in a microspore or pollen cell of said male-fertile parent plant significantly disrupts the metabolism, functioning or development of said microspore or pollen cell;
wherein said foreign DNA is heterozygous at said second genetic locus, and wherein said male-fertile parent plant can be crossed to said male-sterile parent plants to produce, on said male-sterile parent plants, seed which grow into a new generation of male-sterile parent plants.

11. The plant of claim 10, in which said first genetic locus comprising said sterility gene is an endogenous locus comprising a recessive allele in homozygous condition, and in which said restorer gene is the dominant allele at said endogenous locus.

12. The plant of claim 10, in which said first genetic locus is a foreign genetic locus and comprises a foreign male-sterility gene which comprises a sterility DNA under the control of a sterility promoter directing expression selectively in specific stamen cells, and in which said restorer gene at said second genetic locus encodes a protein or polypeptide, which upon expression, inhibits or prevents the phenotypic expression of said male-sterility gene.

13. The plant of claim 12, wherein said sterility promoter directs expression in tapetum cells.

14. The plant of claim 13, wherein said sterility promoter is a TA29 promoter.

15. The plant of claim 10, in which said first DNA encodes a ribonuclease.

16. The plant of claim 15, in which said first DNA encodes a barnase.

17. The plant of claim 10, in which said first promoter is a promoter of a zm13 gene from maize.

18. The plant of any one of claims 10 to 12, in which said plant species is maize.

19. A kit for maintaining a male-sterile line of a plant species, said kit comprising:
   a) a male-sterile line comprising male-sterile parent plants which comprise a male-sterility gene at a first genetic locus, wherein said male-sterility gene is homozygous at said first genetic locus; and,
   b) a maintainer line comprising male-fertile parent plants which comprise said homozygous male-sterility gene at said first genetic locus, and which further comprise, at a second genetic locus which segregates independently from said first genetic locus, a foreign DNA comprising:
      (i) a restorer gene which, upon expression, inhibits or prevents the phenotypic expression of said male-sterility gene, and
      (ii) a pollen-lethality gene comprising, under the control of a first promoter that directs expression selectively in a microspore and/or pollen cell of said male-fertile parent plants, a first DNA encoding a first protein or polypeptide which, when produced in said microspore or pollen cell of said male-fertile parent plants, significantly disrupts the metabolism, functioning or development of said microspore or pollen cell;
   wherein said foreign DNA is heterozygous at said second genetic locus; and
      wherein said male-sterile and male-fertile parent plants can be crossed to produce, on said male-sterile plants, seeds which grow into a new generation of male-sterile parent plants.

20. The kit of claim 19, in which said first genetic locus comprising said sterility gene is an endogenous locus comprising a recessive allele in homozygous condition, and in which said restorer gene is the dominant allele at said endogenous locus.

21. The kit of claim 19, wherein said first genetic locus is a foreign genetic locus and comprises a foreign male-sterility gene which comprises a sterility DNA under the control of a sterility promoter directing expression selectively in specific stamen cells, and in which said restorer gene at said second genetic locus encodes a protein or polypeptide, which upon expression, inhibits or prevents the phenotypic expression of said male-sterility gene.

22. The kit of claim 21, in which said sterility promoter directs expression in tapetum cells.

23. The kit of claim 22, in which said sterility promoter is a TA29 promoter.

24. The kit of claim 19, in which said first DNA encodes a ribonuclease.

25. The kit of claim 24, in which said first DNA encodes a barnase.

26. The kit of claim 19, in which said first promoter is a promoter of a zm13 gene from maize.

27. The kit of any one of claims 19 to 21, in which said plant species is maize.

28. The process of any one of claims 4 to 8, in which said plant species is maize.

29. The plant of any one of claims 13 to 17, in which said plant species is maize.

30. The kit of any on of claims 22 to 26, in which said plant species is maize.

* * * * *